United States Patent
Engel et al.

[11] Patent Number: 5,939,359
[45] Date of Patent: Aug. 17, 1999

[54] HERBICIDAL PYRAZINE DERIVATIVES

[75] Inventors: Stefan Engel, Wörrstadt; Christoph Nübling, Haßloch; Uwe Kardorff, Mannheim; Jürgen Kast, Böhl-Iggelheim; Wolfgang von Deyn, Neustadt; Peter Plath, Frankenthal; Helmut Walter, Obrigheim; Karl-Otto Westphalen, Speyer; Matthias Gerber, Limburgerhof, all of Germany

[73] Assignee: BASF Aktiengesellschaft, Ludwigshafen, Germany

[21] Appl. No.: 08/776,150

[22] PCT Filed: Jul. 24, 1995

[86] PCT No.: PCT/EP95/02924

§ 371 Date: Mar. 20, 1997

§ 102(e) Date: Mar. 20, 1997

[87] PCT Pub. No.: WO96/03391

PCT Pub. Date: Feb. 8, 1996

[30] Foreign Application Priority Data

Jul. 25, 1994 [DE] Germany ............... 44 26 346

[51] Int. Cl.$^6$ ............... A01N 43/60; C07D 241/24; C07D 413/04; C07D 417/04
[52] U.S. Cl. ............... 504/221; 504/223; 504/225; 504/235; 544/55; 544/96; 544/120; 544/295; 544/405; 544/406; 544/407; 544/408
[58] Field of Search ............... 544/405, 406, 544/407, 408, 295, 120, 55, 96; 504/235, 225, 221, 223

[56] References Cited

U.S. PATENT DOCUMENTS

| 3,121,716 | 2/1964 | Yoshida et al. ............... 260/250 |
| 4,460,403 | 7/1984 | Takematsu et al. ............... 71/93 |
| 4,518,599 | 5/1985 | Johnston ............... 544/408 |
| 5,759,956 | 6/1998 | Niedermann et al. ............... 504/235 |

FOREIGN PATENT DOCUMENTS

| 1484049 | 8/1977 | United Kingdom . |
| 9427974 | 12/1994 | WIPO . |

OTHER PUBLICATIONS

Nobuhiro et al., Journal of the Chemical Society, Perkin Transactions 1, pp. 15–19 (1993).
Foks et al., Chemical Abstracts, vol. 88, No. 25, p. 758 (1978).
Foks et al., Chemical Abstracts, vol. 90, No. 28, p. 583 (1979).
*Advanced Organic Chemistry* by Jerry March (2nd Ed.), pp. 382–387 (1977).
Niedermann et al, *Chemical Abstracts*, vol. 122, No. 187621 (Abstract for WO 94,27974, Dec. 8, 1994) (1995).
Dlabal et al, Collect. Czech. Commun. 58 pp. 452–454 (1993).
Ksepko et al, *Chemical Abstracts* vol. 93, No. 46589 (1980).

Primary Examiner—Emily Bernhardt
Attorney, Agent, or Firm—Keil & Weinkauf

[57] ABSTRACT

Substituted pyrazine derivatives of the general formula I

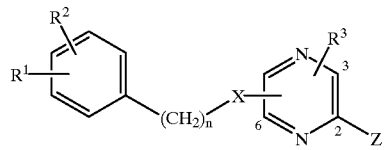

where
X is an oxygen or sulfur atom or a sulfoxyl or sulfonyl group;
n is 0, 1 or 2;
Z is a group

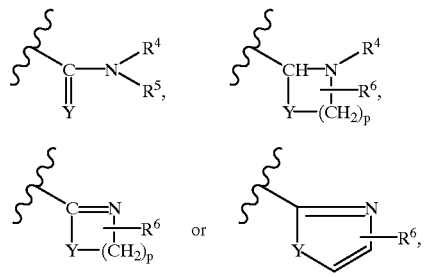

where Y is oxygen or sulfur, $R^6$ is hydrogen, alkyl, alkoxy, halogen or haloalkyl and p is 0 or 1;
and $R^1$, $R^2$, $R^3$, $R^4$ and $R^5$ have the meanings stated in claim 1,
and agriculturally useful salts of the compounds I are useful in herbicides.

26 Claims, No Drawings

HERBICIDAL PYRAZINE DERIVATIVES

The present invention relates to substituted pyrazine derivatives of the general formula I

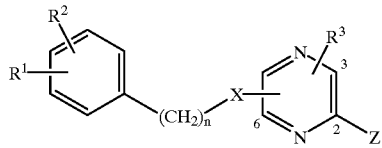

where

X is an oxygen or sulfur atom or a sulfoxyl or sulfonyl group;

n is 0, 1 or 2;

$R^1$ and $R^2$ are identical or different and, independently of one another, are each hydrogen, $C_1$–$C_{12}$-alkyl, $C_2$–$C_{12}$-alkenyl, $C_2$–$C_{12}$-alkynyl or phenyl, where the phenyl group may be monosubstituted or polysubstituted by a low molecular weight radical selected from the group consisting of alkyl, alkenyl, alkynyl, hydroxyl, alkoxy, alkenyloxy, alkynyloxy, alkoxycarbonyl, aminocarbonyl, mono- and dialkylamido and mono- and diarylamido and N-alkyl-N-arylamido, where the alkyl and aryl radicals may be identical or different, halogen, haloalkyl, halo-alkoxy, thio, alkylthio, alkenylthio, alkynylthio, halo-alkylthio, amino, mono- and dialkylamino, N-alkyl-N-arylamino and mono- and diarylamino, where the alkyl and aryl radicals may be identical or different, sulfonyl- and sulfinylalkyl and sulfonyl- and sulfinylaryl, alkoxycarbonylamino, cyano and nitro;

$R^1$ and $R^2$, independently of one another, are each furthermore a five-membered or six-membered N—, O— and/or S-containing heteroaromatic group which may carry one of the abovementioned low molecular weight radicals bonded via a carbon atom, or are each $C_3$–$C_8$-cycloalkyl or an aralkyl or alkaryl group, each having 1 to 6 carbon atoms in the alkyl moiety; $R^1$ and $R^2$, independently of one another, are each also halogen, $C_1$–$C_{12}$-haloalkyl, hydroxyl, $C_1$–$C_{12}$-alkoxy, $C_1$–$C_{12}$-haloalkoxy, $C_2$–$C_{12}$-alkenyloxy, $C_2$–$C_{12}$-alkynyloxy, thio, $C_1$–$C_{12}$-alkylthio, $C_2$–$C_6$-alkenylthio, $C_2$–$C_6$-alkynylthio, $C_1$–$C_6$-alkoxycarbonyl, amino or $C_1$–$C_6$-mono- or dialkyl- or mono- or diarylamino or N-alkyl-N-arylamino, where the alkyl and aryl radicals may be identical or different, $C_1$–$C_6$-mono- or dialkyl- or mono- or diarylamido or N-alkyl-N-arylamido, where the alkyl and aryl radicals may be identical or different, or are each $C_1$–$C_6$-alkylsulfonyl or $C_1$–$C_6$-alkylsulfinyl, arylsulfonyl or arylsulfinyl, cyano or nitro;

$R^3$ is hydrogen or halogen, $C_1$–$C_{12}$-alkyl, $C_1$–$C_2$-haloalkyl, hydroxyl, $C_1$–$C_{12}$-alkoxy, thio or $C_1$–$C_{12}$-alkylthio, amino or mono- or dialkylamino or mono- or diarylamino or N-alkyl-N-arylamino, each of which has 1 to 6 carbon atoms per alkyl radical; and

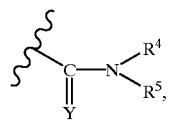 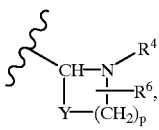

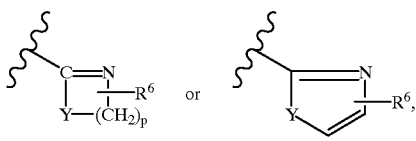

where Y is oxygen or sulfur, p is 2 or 3 and $R^6$ is hydrogen, $C_1$–$C_4$-alkyl, $C_1$–$C_4$-alkoxy, halogen or $C_1$–$C_4$-haloalkyl;

$R^4$ is hydrogen, $C_1$–$C_{12}$-alkyl, $C_2$–$C_{12}$-alkenyl, $C_2$–$C_{12}$-alkynyl or phenyl, where the phenyl group may be monosubstituted or polysubstituted by a low molecular weight radical selected from the group consisting of alkyl, alkenyl, alkynyl, hydroxyl, alkoxy, alkenyloxy, alkynyloxy, alkoxycarbonyl, aminocarbonyl, mono- and dialkylamido and mono- and diarylamido and N-alkyl-N-arylamido, where the alkyl and aryl radicals may be identical or different, halogen, haloalkoxy, thio, alkylthio, alkenylthio, alkynylthio, haloalkylthio, amino, mono- and dialkylamino, N-alkyl-N-arylamino and mono- and diarylamino, where the alkyl and aryl radicals may be identical or different, sulfonyl- and sulfinylalkyl and sulfonyl- and sulfinylaryl, alkoxycarbonylamino, cyano and nitro;

$R^4$ is furthermore $C_3$–$C_8$-cycloalkyl, $C_5$–$C_8$-cycloalkenyl or phenyl-$C_1$–$C_6$-alkyl, where the phenyl group in turn may be monosubstituted or polysubstituted by a low molecular weight radical as stated above;

$R^4$ is furthermore alkaryl having 1 to 6 carbon atoms in the alkyl moiety, or halogen, $C_1$–$C_{12}$-haloalkyl, $C_2$–$C_{12}$-haloalkenyl or $C_2$–$C_{12}$-haloalkynyl;

$R^5$ is $C_1$–$C_{12}$-alkyl, $C_2$–$C_{12}$-alkenyl, $C_2$–$C_{12}$-alkynyl or phenyl, where the phenyl group may be monosubstituted or polysubstituted by a low molecular weight radical selected from the group consisting of alkyl, alkenyl, alkynyl, hydroxyl, alkoxy, alkenyloxy, alkynyloxy, alkoxycarbonyl, aminocarbonyl, mono- and dialkylamido and mono- and diarylamido and N-alkyl-N-arylamido, where the alkyl and aryl radicals may be identical or different, halogen, haloalkyl, haloalkoxy, thio, alkylthio, alkenylthio, alkynylthio, haloalkylthio, amino, mono- and dialkylamino, N-alkyl-N-arylamino and mono- and diarylamino, where the alkyl and aryl radicals may be identical or different, sulfonyl- and sulfinylalkyl and sulfonyl- and sulfinylaryl, alkoxycarbonylamino, cyano and nitro;

$R^5$ is furthermore a five-membered or six-membered N—, O— and/or S-containing heteroaromatic group which may carry one of the abovementioned low molecular weight radicals bonded via a carbon atom, or $C_3$–$C_8$-cycloalkyl or an alkylphenyl or phenylalkyl group, each having 1 to 6 carbon atoms in the alkyl moiety, where the phenyl group in turn may be monosubstituted or polysubstituted by a low molecular weight radical as stated above in the case of $R^4$;

$R^5$ is furthermore $C_1$–$C_{12}$-haloalkyl, hydroxyl, $C_1$–$C_{12}$-alkoxy, $C_1$–$C_{12}$-haloalkoxy, $C_2$–$C_{12}$-alkenyloxy, $C_2$–$C_{12}$-alkynyloxy, thio, $C_1$–$C_{12}$-alkylthio, $C_2$–$C_{12}$-alkenylthio-, $C_2$–$C_{12}$-alkynylthio, $C_1$–$C_6$-alkoxycarbonyl, amino or $C_1$–$C_6$-mono- or dialkyl- or mono or diarylamino or N-alkyl-N-arylamino, where the alkyl and aryl radicals may be identical or different, $C_1$–$C_6$-mono- or dialkyl- or mono- or diarylamido or N-alkyl-N-arylamido, where the alkyl and aryl radicals may be identical or different, $C_3$–$C_6$-cycloalkyl, $C_3$–$C_6$-cycloalkyl-$C_1$–$C_4$-alkyl, $C_5$–$C_8$-cycloalkenyl, phenyl-$C_1$–$C_4$-alkyl, tri-$C_1$–$C_4$-alkylsilyl, $C_1$–$C_4$-alkylcarbonyl-$C_1$–$C_4$-alkoxy, $C_1$–$C_4$-alkylcarbonyl, methylcarbonyl-$C_1$–$C_4$-alkoxy or $C_1$–$C_4$-methylcarbonyl, where the two last mentioned radicals may each be substituted at the methylene group by $C_1$–$C_5$-aminoalkyl, $C_1$–$C_5$-hydroxyalkyl, $C_1$–$C_5$-thioalkyl or $C_1$–$C_5$-carboxylalkyl;

$R^4$ and $R^5$ together form a $C_3$–$C_8$-alkylene chain which may be interrupted by an oxygen or sulfur atom or by an amino, $C_1$–$C_6$-alkylamino or arylamino group or may form a $C_5$–$C_8$-alkenylene group which may be interrupted by an oxygen or sulfur atom or by an amino, $C_1$–$C_6$-alkylamino or arylamino group;

with the exception of 2-phenylthiopyrazine-6-hydrazide and 2-phenylthiopyrazine-6-hydroxamic acid, and with the proviso that, when X is O, n is 0 and Z is

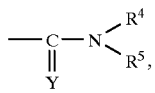

X is not bonded to the pyrazine ring in the 6-position, or, when X is bonded to the pyrazine ring in the 6-position, $R^1$ and $R^2$, independently of one another, are each hydrogen or a five-membered or six-membered N—, O— and/or S-containing heteroaromatic group which may carry one of the abovementioned low molecular weight radicals bonded via a carbon atom, or are each $C_3$–$C_8$-cycloalkyl or an aralkyl or alkaryl group, each having 1 to 6 carbon atoms in the alkyl moiety, both radicals $R^1$ and $R^2$ not simultaneously being hydrogen;

and agriculturally useful salts of the compounds I and the use of the compounds I and IV (Z=CN) as herbicides.

From the work of A. D. Gutman (W. J. Michaely and A. D. Gutman, Synthesis and Chemistry of Agrochemicals in American Chemical Society Symp. Series, Chapter 5, 1987), it is known that 2-phenoxynicotinamides constitute a class of compounds having pronounced herbicidal activity.

Furthermore, the herbicidal activity of 2-phenoxypicolinamides is disclosed in EP-A-0 447 004, EP-A-0 488 474, EP-A-0 537 861, EP-A-572 093 and WO 94/08991.

Pyrazine derivatives have to date attracted only little interest as active ingredients. Some pyrazine dicarboxamides have been described in JP 94/077367 as herbicidal compounds or, according to JP 94/08607, serve as intermediates for the preparation of crop protection agents. Some 2-phenylthio- and 2-benzylthio-6-cyanopyrazines, 2-phenylthiopyrazine-6-hydrazides and 2-phenylthiopyrazine-6-hydroxamic acids have been investigated as tuberculostatic agents (H. Foks, H. Jancwiec and M. Zielenicki, Pd. J. Pharmacol. Pharm. 29 (1977), 663–673).

Wo 94/27974 describes pyrimidine, pyrazine and triazine derivatives having specific substitution as herbicides.

However, the herbicidal activity of the known compounds is only partly satisfactory, there being a poor effect in the pre-emergence and postemergence methods. It is an object of the present invention to provide novel pyrazine derivatives which have high herbicidal activity and at the same time can be widely used.

We have found that this object is achieved by the pyrazine derivatives of the formula I which are defined at the outset.

We have also found that the corresponding pyrazine derivatives having a cyano group instead of the group Z (compounds IV) also have very good herbicidal activity. At the same time, these compounds IV serve as intermediates for the synthesis of the pyrazines I.

The present invention furthermore relates to herbicides containing the compounds I and to the use of the compounds I and IV as herbicides.

Unless specified specifically, the general radicals used in the formula I have the following meanings above: low molecular weight radical is to be understood as meaning a radical of up to 8, in particular up to 4, carbon atoms per group. A low molecular weight dialkylamino group would be, for example, di-($C_1$–$C_4$-)-alkylamino, such as dibutylamino. Halogen or halo is in particular fluorine, chlorine or bromine. Aryl is preferably unsubstituted phenyl or naphthyl, or phenyl or naphthyl, each of which is monosubstituted to pentasubstituted by halogen or monosubstituted to trisubstituted by $C_1$–$C_4$-alkyl, $C_1$–$C_4$-haloalkyl, $C_2$–$C_4$-alkenyl, $C_2$–$C_4$-alkynyl, hydroxyl, $C_1$–$C_4$-alkoxy, $C_2$–$C_4$-alkenoxy, $C_2$–$C_4$-alkynyloxy, $C_1$–$C_4$-alkoxycarbonyl, mono- or dialkylamido, mono- or diarylamido, N-alkyl-N-arylamido, where the alkyl and aryl radicals may be identical or different, thio, $C_1$–$C_4$-alkylthio, $C_2$–$C_4$-alkenylthio, $C_2$–$C_4$-alkynylthio, $C_1$–$C_4$-halo-alkylthio amino, mono- or $C_1$–$C_4$-dialkylamino or mono- or diaryl-amino, N-alkyl-N-arylamino, where the alkyl and aryl radicals may be identical or different, $C_1$–$C_4$-sulfonyl- or $C_1$–$C_4$-sulfinylalkyl- or sulfonyl- or sulfinylaryl, $C_1$–$C_4$-alkoxycarbonylamino, cyano or nitro.

With regard to the biological activity, compounds I or IV which carry a radical

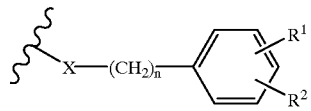

in the 2- or 3-position are preferred. 2-Phenoxypyrazine-3-carboxamides and 2-phenoxypyrazine-6-carboxamides, each unsubstituted or substituted by $R^1$, $R^2$, $R^3$, $R^4$ and $R^5$, are particularly preferred.

Compounds of the formula I where Z is a group

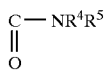

are also preferred. $R^3$ is preferably hydrogen. $R^4$ is likewise preferably hydrogen or $C_1$–$C_4$-alkyl, eg. methyl. $R^5$ is preferably an unsubstituted or substituted $C_1$–$C_6$-alkyl or phenyl radical, eg. methyl, ethyl, propyl, isopropyl, butyl, sec-butyl, tert-butyl, trifluoromethyl, 2,2,2-trifluoroethyl or phenyl, unsubstituted or monosubstituted to trisubstituted by fluorine, chlorine, fluoro-$C_1$–$C_2$-alkyl such as trifluoromethyl, or chloro-$C_1$–$C_4$-alkyl, such as trichloromethyl.

Other preferred compounds of the formulae I and IV are those in which:

Z is a group

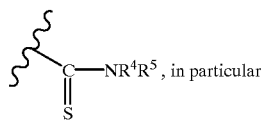, in particular 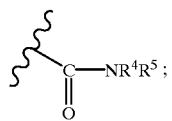;

X and Y are each an oxygen or sulfur atom, particularly preferably an oxygen atom;

n is either 0 or 1, particularly preferably 0;

$R^1$ and $R^2$ may be identical or different and, independently of one another, are each hydrogen or straight-chain or branched $C_1$–$C_{12}$-alkyl, in particular $C_1$–$C_6$-alkyl, for example methyl, ethyl, n-propyl, isopropyl, n-butyl, sec-butyl or tert-butyl, straight-chain or branched $C_2$–$C_{12}$-alkenyl, particularly preferably $C_2$–$C_6$-alkenyl, for example allyl, straight-chain or branched $C_2$–$C_{12}$-alkynyl, particularly preferably $C_2$–$C_6$-alkynyl, for example propargyl, aryl, particularly preferably phenyl, where the aryl group in turn may be monosubstituted or polysubstituted, for example monosubstituted to trisubstituted, in various ring positions by a low molecular weight alkyl, alkenyl, alkynyl, hydroxyl, alkoxy, alkenyloxy, alkynyloxy or alkoxycarbonyl group, amido, mono- or dialkylamido or mono- or diarylamido or N-alkyl-N-arylamino, where the alkyl and aryl radicals, in particular unsubstituted or substituted phenyl radicals, may be identical or different, halogen or haloalkoxy, thio, alkylthio, alkenylthio, alkynylthio, haloalkylthio, amino, mono- or dialkylamino or N-alkyl-N-arylamido or mono- or diarylamino, where the alkyl and aryl radicals may be identical or different, sulfonyl- or sulfinylalkyl or sulfonyl- or sulfinylaryl, alkoxycarbonylamino, cyano or nitro. $R^1$ and $R^2$, independently of one another, are each furthermore a five-membered or six-membered N—, O— or S-containing hetaryl group, in particular pyridine, pyrimidine, furan, pyrrole, pyrazole, imidazole, oxazole, isoxazole, thiazole, isothiazole or thiophene, where the hetaryl radical may carry, bonded via carbon, a low molecular weight radical, for example halogen, $C_1$–$C_4$-alkyl, $C_1$–$C_4$-haloalkyl, $C_2$–$C_4$-alkenyl, $C_2$–$C_4$-alkynyl, hydroxyl, $C_1$–$C_4$-alkoxy, $C_2$–$C_4$-alkenyloxy, $C_2$–$C_4$-alkynyloxy, $C_1$–$C_4$-alkoxycarbonyl, mono- or dialkylamido, mono- or diarylamido or N-alkyl-N-arylamido, where the alkyl and aryl radicals may be identical or different, thio, $C_1$–$C_4$-alkylthio, $C_2$–$C_4$-alkenylthio, $C_2$–$C_4$-alkynylthio, $C_1$–$C_4$-haloalkylthio, amino, mono- or $C_1$–$C_4$-dialkylamino or mono- or diarylamino, N-alkyl-N-arylamino, where the alkyl and aryl radicals may be identical or different, $C_1$–$C_4$-sulfonyl- or $C_1$–$C_4$-sulfinylalkyl or sulfonyl- or sulfinylaryl, $C_1$–$C_4$-alkoxycarbonylamino, cyano or nitro, or $R^1$ and $R^2$ are each $C_3$–$C_8$-cycloalkyl, particularly preferably cyclopropyl, cyclobutyl, cyclopentyl or cyclohexyl, $C_1$–$C_6$-alkaryl, eg. phenyl, substituted by 1 to 3 methyl radicals, in particular tolyl, $C_1$–$C_6$-alkyl, for example benzyl or phenylethyl. $R^1$ and $R^2$ independently of one another are each also halogen, preferably fluorine, chlorine or bromine, in particular fluorine or chlorine, or straight-chain or branched $C_1$–$C_{12}$-haloalkyl, particularly preferably $C_1$–$C_6$-halo-alkyl, in particular trifluoromethyl, trichloromethyl, trichloroethyl or trifluoroethyl, hydroxyl, straight-chain or branched $C_1$–$C_{12}$-alkoxy, in particular $C_1$–$C_6$-alkoxy, for example methoxy or ethoxy, straight-chain or branched $C_1$–$C_{12}$-haloalkoxy, particularly preferably $C_1$–$C_6$-haloalkoxy, for example trifluoromethoxy, straight-chain or branched $C_2$–$C_{12}$-alkenyloxy, particularly preferably $C_2$–$C_6$-alkenyloxy, for example allyloxy, $C_2$–$C_{12}$-alkynyloxy, particularly preferably $C_2$–$C_6$-alkynyloxy, thio, straight-chain or branched $C_1$–$C_{12}$-alkylthio, in particular $C_1$–$C_6$-alkylthio, $C_2$–$C_{12}$-alkenylthio, particularly preferably $C_2$–$C_6$-alkenylthio, $C_2$–$C_6$-alkynylthio, $C_1$–$C_6$-alkoxycarbonyl, amino or $C_1$–$C_6$-mono- or di-($C_1$–$C_6$)-alkyl- or mono- or diarylamino or N-$C_1$–$C_6$-alkyl-N-arylamino, where the alkyl and aryl radicals may be identical or different, $C_1$–$C_6$-mono- or dialkyl- or mono- or diarylamido, where the alkyl and aryl radicals may be identical or different, $C_1$–$C_6$-alkylsulfonyl or $C_1$–$C_6$-sulfinyl or arylsulfonyl or arylsulfinyl, cyano or nitro;

$R^3$ is hydrogen, halogen, particularly preferably fluorine, chlorine or bromine, $C_1$–$C_{12}$-alkyl, particularly preferably $C_1$–$C_6$-alkyl, $C_1$–$C_{12}$-haloalkyl, in particular $C_1$–$C_6$-haloalkyl, for example trifluoromethyl or trichloroethyl, hydroxyl, $C_1$–$C_2$-alkoxy, particularly preferably $C_1$–$C_6$-alkoxy, such as methoxy or ethoxy, thio or $C_1$–$C_{12}$-alkylthio, particularly preferably $C_1$–$C_6$-alkylthio, amino, $C_1$–$C_6$-mono- or dialkyl- or mono- or diarylamino or N-alkyl-N-arylamino, a preferred aryl radical being phenyl;

$R^4$ is hydrogen or $C_1$–$C_{12}$-alkyl, in particular $C_1$–$C_6$-alkyl, for example methyl, ethyl, n-propyl, isopropyl, n-butyl, sec-butyl or tert-butyl, straight-chain or branched $C_2$–$C_{12}$-alkenyl, particularly preferably $C_2$–$C_6$-alkenyl, for example allyl, straight-chain or branched $C_2$–$C_{12}$-alkynyl, in particular $C_2$–$C_6$-alkynyl, for example propargyl, or aryl, particularly preferably phenyl, where the aryl group in turn may be monosubstituted or polysubstituted in various ring positions by a low molecular weight alkyl, alkenyl, alkynyl, hydroxyl, alkoxy, alkenyloxy, alkynoxy or alkoxycarbonyl group, aminocarbonyl, mono- or dialkylamido or mono- or diarylamido, where the alkyl and aryl radicals may be identical or different, halogen or haloalkoxy, thio, alkylthio, alkenylthio, alkynylthio, haloalkylthio, amino, mono- or dialkylamino, N-alkyl-N-arylamino or mono- or diarylamino, where the alkyl and aryl radicals may be identical or different, sulfonyl- or sulfinylalkyl or sulfonyl- or sulfinylaryl, alkoxycarbonylamino, cyano or nitro. $R^4$ is furthermore $C_3$–$C_8$-cycloalkyl, particularly preferably cyclopropyl, cyclobutyl, cyclopentyl or cyclohexyl, $C_3$–$C_8$-cycloalkylalkyl, preferably $C_3$–$C_6$-cycloalkylalkyl, $C_5$–$C_8$-cycloalkenyl, in particular $C_5$- or $C_6$-cycloalkenyl, $C_1$–$C_6$-aralkyl, particularly preferably phenylalkyl, where the aryl group in turn may be monosubstituted or polysubstituted, in particular monosubstituted to tri-substituted, in various ring positions by a low molecular weight alkyl, alkenyl, alkynyl, hydroxyl, alkoxy, alkenyloxy, alkynyloxy or alkoxycarbonyl group, mono- or dialkylamido, such as methylamino or dimethylamino, or mono- or diarylamido, such as phenylamino or diphenylamino, or N-alkyl-N-arylamino such as N-methyl-N-phenylamino, where the alkyl and aryl radicals may be identical or different, halogen or haloalkoxy, thio, alkylthio, alkenylthio, alkynylthio, haloalkylthio, amino, mono or dialkylamino or mono- or diarylamino, where the alkyl and aryl radicals may be identical or different, sulfonyl- or sulfinylalkyl or sulfonyl- or sulfinylaryl, alkoxycarbonylamino, cyano, or nitro. $R^4$ is also $C_1$–$C_6$-alkaryl, for example phenyl, substituted by 1 to 3 methyl radicals, eg. tolyl, or halogen, particularly preferably fluorine, chlorine or bromine. $R^4$ is furthermore $C_1$–$C_{12}$-haloalkyl, particularly preferably $C_1$–$C_6$-haloalkyl, in particular trifluoromethyl, trichloromethyl or trifluoroethyl, $C_1$–$C_{12}$-haloalkenyl, preferably $C_1$–$C_6$-haloalkenyl, or $C_1$–$C_{12}$-haloalkynyl, in particular $C_1$–$C_6$-haloalkynyl;

$R^5$ is straight-chain or branched $C_1$–$C_{12}$-alkyl, in particular $C_1$–$C_6$-alkyl, for example methyl, ethyl, n-propyl, isopropyl, n-butyl, sec-butyl or tert-butyl, straight-chain or branched $C_2$–$C_{12}$-alkenyl, particularly preferably $C_2$–$C_6$-alkenyl, for example allyl, straight-chain or branched $C_2$–$C_{12}$-alkynyl, particularly preferably $C_2$–$C_6$-alkynyl, for example propargyl, aryl, particularly preferably phenyl, where the aryl group in turn may be monosubstituted or polysubstituted, in particular monosubstituted to trisubstituted, in various ring positions by a low molecular weight radical as stated for $R^4$, for example alkyl, alkenyl, alkynyl, hydroxyl, alkoxy, alkenyloxy, alkynyloxy or alkoxycarbonyl, mono- or dialkylamido, N-alkyl-N-arylamido or mono- or diarylamido, where the alkyl and aryl radicals may be identical or different, halogen or haloalkoxy, thio, alkylthio, alkenylthio, alkynylthio, haloalkylthio, amino, mono- or dialkylamino, N-alkyl-N-arylamino or mono- or diarylamino, where the alkyl and aryl radicals may be identical or different, sulfonyl- or sulfinylalkyl or sulfonyl- or sulfinylaryl, alkoxycarbonylamino, cyano or nitro. $R^5$ is furthermore a five-membered or six-membered N—, O— or S-containing hetaryl group, unsubstituted or substituted as stated for $R^4$, particularly preferably pyridine, pyrimidine, furan, pyrrole, pyrazole, imidazole, oxazole, isoxazole, thiazole, isothiazole or thiophene, or $C_3$–$C_8$-cycloalkyl, particularly preferably cyclopropyl, cyclobutyl, cyclopentyl or cyclohexyl, $C_1$–$C_6$-aralkyl, particularly preferably phenylalkyl, for example benzyl or phenylethyl, where the aryl group in turn may be monosubstituted or polysubstituted in various ring positions by a low molecular weight radical as stated above, for example alkyl, alkenyl, alkynyl, hydroxyl, alkoxy, alkenyloxy, alkynyloxy or alkoxycarbonyl, mono- or dialkylamido, N-alkyl-N-arylamido or mono- or diarylamido, where the alkyl and aryl radicals may be identical or different, halogen or haloalkoxy, thio, alkylthio, alkenylthio, alkynylthio, haloalkylthio, amino, mono- or dialkylamino, N-alkyl-N-arylamino or mono- or diarylamino, where the alkyl and aryl radicals may be identical or different, sulfonyl- or sulfinylalkyl or sulfonyl- or sulfinylaryl, alkoxycarbonyl, cyano or nitro. $R^5$ is also alkaryl, for example tolyl. $R^5$ is furthermore straight-chain or branched $C_1$–$C_{12}$-haloalkyl, particularly preferably $C_1$–$C_6$-haloalkyl, in particular trifluoromethyl, trichloroethyl or trifluoroethyl, hydroxyl, straight-chain or branched $C_1$–$C_{12}$-alkoxy, in particular $C_1$–$C_6$-alkoxy, for example methoxy or ethoxy, straight-chain or branched $C_1$–$C_{12}$-haloalkoxy, particularly preferably $C_1$–$C_6$-haloalkoxy, for example trifluoromethoxy, straight-chain or branched $C_2$–$C_{12}$-alkenyloxy, particularly preferably $C_2$–$C_6$-alkenyloxy, for example allyloxy, $C_2$–$C_{12}$-alkynyloxy, in particular $C_2$–$C_6$-alkynyloxy, thio, straight-chain or branched $C_1$–$C_{12}$-alkylthio, in particular $C_1$–$C_6$-alkylthio, $C_2$–$C_{12}$-alkenylthio, particularly preferably $C_2$–$C_6$-alkenylthio, $C_2$–$C_{12}$-alkynylthio, in particular $C_2$–$C_6$-alkynylthio, $C_1$–$C_6$-alkoxycarbonyl, amino or $C_1$–$C_6$-mono- or dialkyl- or mono- or diarylamino, where the alkyl and aryl radicals may be identical or different, $C_1$–$C_6$-mono- or dialkyl- or mono or diarylamido, where the alkyl and aryl radicals may be identical or different, $C_3$–$C_6$-cycloalkyl, eg. cyclopropyl, cyclopentyl or cyclohexyl, $C_3$–$C_6$-cycloalkyl-$C_1$–$C_4$-alkyl, eg. cyclopropylmethyl or cyclohexylmethyl, $C_5$–$C_8$-cycloalkenyl, eg. cyclohexenyl, phenyl-$C_1$–$C_4$-alkyl, such as benzyl or phenylethyl, tri-$C_1$–$C_4$-alkylsilyl, eg. trimethylsilyl, $C_1$–$C_4$-alkylcarbonyl-$C_1$–$C_4$-alkoxy, such as methylcarbonylmethoxy, $C_1$–$C_4$-alkylcarbonyl, such as methylcarbonyl ($CH_2COOH$), substituted methylcarbonyl-$C_1$–$C_4$-alkoxy or methylcarboxyl, where aminoalkyl, hydroxyalkyl, thioalkyl or carboxylalkyl, each having 1–5 carbon atoms in the alkyl moiety, are suitable as substituents and the functional group (amino, hydroxyl, thio or COOH) is preferably bonded as a terminal group.

$R^4$ and $R^5$ together form a $C_3$–$C_8$-alkylene chain or a $C_5$–$C_8$-alkenyl chain, particularly preferably a $C_3$–$C_6$-alkylene chain, very particularly. preferably a $C_5$- or $C_6$-alkenylene group, where the chains may each be interrupted by an oxygen or sulfur atom or by an amino or $C_1$–$C_6$-monoalkylamino or monoarylamino group. For example, $R^4$ and $R^5$, together with the N atom to which they are bonded, form a morpholine, piperidyl, piperazinyl, pyrrolidinyl or pyrrolinyl radical.

Preferred compounds of the formula I where $Z \neq C(=Y)NR^4R^5$ are those in which n, X, $R^1$, $R^2$ and $R^3$ have the abovementioned meanings and Z is selected from the following heterocyclic radicals:

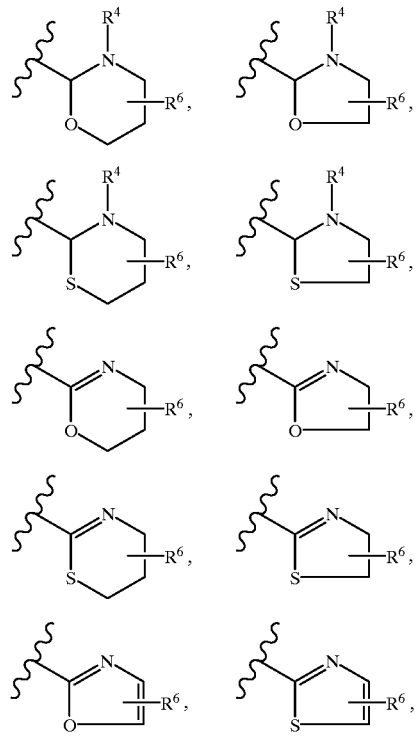

where $R^4$ is preferably a low molecular weight alkyl radical, such as methyl, or in particular hydrogen and $R^6$ is preferably methyl, ethyl, hydrogen, isopropyl, n-propyl, butyl, tert-butyl or one of the corresponding alkoxy radicals, halogen, such as bromine, chlorine or fluorine, or $C_1$–$C_4$-haloalkyl, in particular $C_1$–$C_2$-haloalkyl, such as trifluoromethyl or trichloromethyl.

Preferred compounds of the formula IV are those in which n, X, $R^1$, $R^2$ and $R^3$ are as defined in formula I.

The compounds I and IV may also be present in the form of their agriculturally useful salts, the type of salt generally being unimportant. Suitable salts are usually those of bases which do not adversely affect the herbicidal action of I and IV.

Particularly suitable basic salts are those of the alkali metals, preferably the sodium and potassium salts, those of the alkaline earth metals, preferably calcium, magnesium and barium salts, and those of the transition metals, preferably manganese, copper, zinc and iron salts, and the ammonium salts which may carry from one to three $C_1$–$C_4$-alkyl substituents, hydroxy-$C_1$–$C_4$-alkyl substituents and/or a phenyl or benzyl substituent, preferably diisopropylammonium, tetramethylammonium, tetrabutylammonium, trimethylbenzylammonium and trimethyl(2-hydroxyethyl)ammonium salts, the phosphonium salts, the sulfonium salts, preferably tri-$C_1$–$C_4$-alkylsulfonium salts, and the sulfoxonium salts, preferably tri-$C_1$–$C_4$-alkylsulfoxonium salts.

The compounds I in which

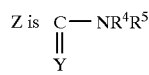

are prepared, for example, by reacting pyrazine derivatives of the general formula II

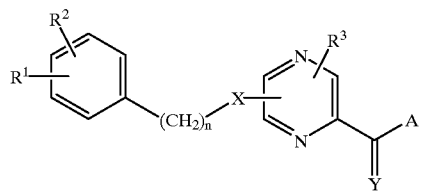

where n, X, Y, $R^1$, $R^2$ and $R^3$ have the abovementioned meanings and A is a suitable leaving group, with an amine of the general formula III

where $R^4$ and $R^5$ have the abovementioned meanings, either in the presence of an acid acceptor (Houben-Weyl, Vol. 8, Georg Thieme-Verlag, Stuttgart 1952, pages 647–672) or of a coupling reagent typical for forming an amide bond (M. Bodansky, Principles of Peptide Synthesis, Springer Verlag, Berlin 1984, pages 16–58).

Suitable acid acceptors are inorganic bases, such as sodium carbonate or potassium carbonate, sodium methylate, sodium ethylate, sodium hydride or organic bases, such as triethylamine or pyridine. The latter may simultaneously serve as a solvent.

A leaving group A is any group which can be eliminated from the starting material of the general formula II under reaction conditions conventionally used for amidations. The leaving group A is therefore preferably halogen, such as bromine or in particular chlorine, or alkoxy, particularly preferably $C_1$–$C_4$-alkoxy, for example methoxy, or imidazolyl.

The substituted amines of the general formula III are known or can be prepared by conventional processes.

Typical coupling reagents from peptide synthesis may also be used for forming the amide bond. Preferred coupling reagents are, for example, dicyclohexylcarbodiimide (DCC), N'-(3-dimethylaminopropyl)-N-ethylcarbodiimide (DIC), ethyl 1,2-dihydro-2-ethoxyquinoline-1-carboxylate (EEDQ), isobutyl 1,2-dihydro-2-isobutoxy-1-quinolinecarboxylate (IIDQ), 1-benzotriazolyloxytris(dimethylamino)phosphonium hexafluorophosphate (BOP), O-benzotriazol-1-yl-,N,N,N',N'-tetramethyluronium hexafluorophosphate (HBTU), O-[(cyano(ethoxycarbonyl)methylidene)amino]-1,1,3,3-tetramethyluronium tetrafluoroborate (TOTU), propanephosphonic anhydride (PPA) and 3-dimethylaminophosphinothioyl-2(3H)-oxazolone (MPTO).

The amidation is preferably carried out in the presence of an inert organic solvent, for example dimethylformamide or dimethyl sulfoxide, or of an organic hydrocarbon, such as benzene or toluene, of a halohydrocarbon, preferably dichloromethane, of an ether, in particular diethyl ether, or of an ester, for example ethyl acetate, at from 0 to 100° C., preferably from 0 to 50° C.

The starting materials are usually reacted with one another in stoichiometric amounts. However, it may be advantageous to use one of the starting materials in an excess of from 0.1 to 10 mol equivalents, for example for increasing the yield.

The compounds of the general formula II are either prepared by acidic or alkaline hydrolysis of pyrazine derivatives of the formula IV

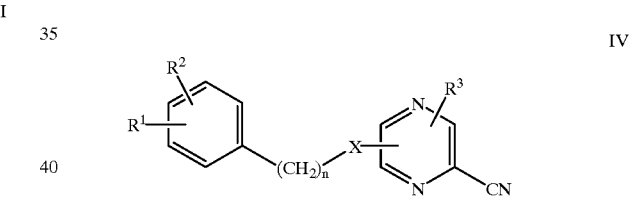

where n, X, $R^1$, $R^2$ and $R^3$ have the abovementioned meanings, from the initially formed pyrazine derivatives of the general formula V,

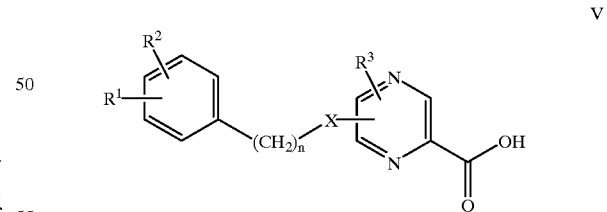

where n, X, $R^1$, $R^2$ and $R^3$ have the meanings described above, by subsequent conventional processes, or are directly converted by conventional processes into the pyrazine derivatives of the general formula II (C. Ferri, Reaktionen der organischen Synthese, Georg Thieme-Verlag, Stuttgart 1978, pages 432–461).

The preparation of the pyrazine derivatives of the general formula V is carried out in the presence of an inert solvent, for example water or ethylene glycol, using suitable acids, for example hydrochloric acid, sulfuric acid or phosphoric acid, or suitable bases, for example potassium hydroxide or sodium hydroxide, at from 0 to 150° C., while the direct preparation of the pyrazine derivatives of the general formula II is preferably carried out by acidic hydrolysis in the presence of a suitable reactant, for example methanol, under the reaction conditions described above.

The pyrazine derivatives of the general formula IV are obtainable by reacting the metal salts of the alcohols of the general formula VI

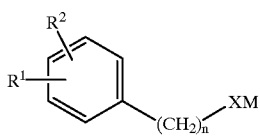

VI where n, X, $R^1$ and $R^2$ have the meanings described above and M is a metal, for example an alkali metal or alkaline earth metal, with the pyrazine derivatives of the general formula VII,

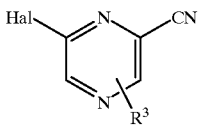

VII where $R^3$ has the abovementioned meanings and Hal is halogen, preferably chlorine or bromine, in the presence of an inert organic solvent (H. Foks, M. Janowiec, Acta Pol. Pharm. 35 (1978), 143–147).

The metal salts of the alcohols of the general formula VI are preferably alkali metal salts, such as the sodium or potassium salt. They are prepared by reacting the alcohols with suitable metal bases, for example with the metal carbonates or hydrides. A preferred metal salt is sodium salt, which is prepared using sodium hydride.

The choice of the organic solvent depends on the starting materials used. In general, any polar, organic solvent, for example dimethylformamide or tetrahydrofuran, is suitable.

The starting materials are usually reacted with one another in stoichiometric amounts. However, it may be advantageous to use one of the starting materials in an excess of from 0.1 to 10 mol equivalents, for example in order to increase the yield.

The pyrazine derivatives of the general formula VII are prepared starting from the pyrazine derivatives of the general formula VIII

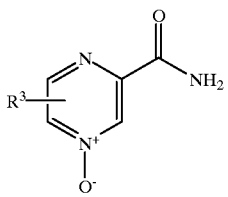

VIII where $R^3$ has the abovementioned meanings, by reaction with phosphoryl halides, preferably phosphoryl chloride or phosphoryl bromide, as reported by B. Klein, N. E. Hetman and M. E. O'Donnel (J. Org. Chem. 28 (1963), 1682–1686).

The pyrazine derivatives of the formula VIII are known or can be prepared in the manner described by H. Foks and J. Sawlewicz in Acta Polon. Pharm. 21 (1964), 429–436.

The novel compounds of the general formula I, where Z is a group

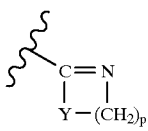

and n, p, X, Y, $R^1$, $R^2$ and $R^3$ have the meanings described in claim 1, can be prepared, for example, starting from pyrazine derivatives of the general formula I, where Z is a group

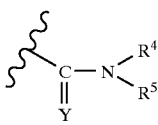

for example the pyrazine derivatives of the formula IX

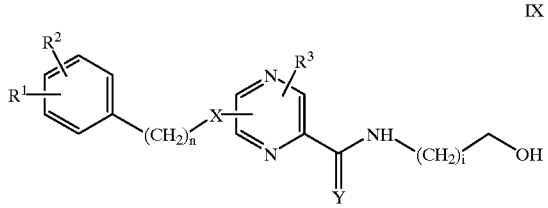

IX where 1 is 1 or 2, in the presence of thionyl chloride (W. S. Johnson and E. N. Schubert, J. Am. Chem. Soc. 72 (1950), 2187–2190). The desired pyrazine derivatives are subsequently liberated by treating the resulting hydrochlorides II with dilute hydrochloric acid.

The novel compounds of the general formula I, where Z is a group

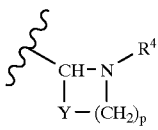

and n, p, X, Y, $R^1$, $R^2$, $R^3$ and $R^4$ have the meanings described in claim 1, are prepared, for example, by reacting the pyrazine derivatives of the general formula X

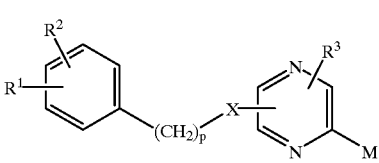

X where M is a metal, for example an alkali metal, such as sodium, with compounds of the general formula XI

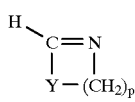

XI where p and Y have the meanings described in claim 1 (A. I. Meyers and H. W. Adickes, Tetrahedron Lett. (1969) 5151–5154). $R^4$ may be introduced by reacting the intermediate XII

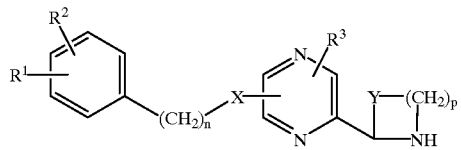

XII with compounds of the general formula XIII, $R^4$—Hal    XIII where Hal is halogen, for example bromine, in the presence of a base.

The compounds of the general formula I, where Z is a group

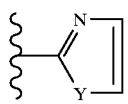

and n, p, X, Y, $R^1$, $R^2$ and $R^3$ have the meanings described in claim 1, are prepared, for example, by coupling the stannyl compounds XIV

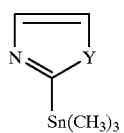

XIV with pyrazine derivatives of the general formula XV

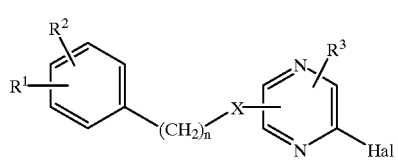

XV where Hal is halogen, preferably bromine, in the presence of a suitable palladium catalyst (T. R. Bailey, Tetrahedron Lett. 27 (1986), 4407–4410). The synthesis of the stannyl compounds of the formula XIV can be carried out, for example, starting from correspondingly metallated compounds by methods known from the literature (T. R. Kelly, C. T. Jagoe and Z. Gu, Tetrahedron Lett. 32 (1991), 4263–4266).

The pyrazine derivatives of the formula XV can be prepared by methods similar to that for the synthesis of the compound IV, starting from 2,6-dichloropyrazine.

Examples of particularly preferred compounds of the general formula I are listed in the tables below. The definitions of the radicals are not particularly preferred only in the special combination of radicals but also for each radical considered in isolation.

TABLE 1

$Z = C \parallel O$
$X = S$
$n = 0$
$R^3 = H$

I.1

| $R^1$ | $R^2$ | $R^4$ | $R^5$ |
|---|---|---|---|
| H | 3-CF$_3$ | H | CH$_3$ |
| H | 3-CF$_3$ | H | C$_2$H$_5$ |
| H | 3-CF$_3$ | H | n-C$_3$H$_7$ |
| H | 3-CF$_3$ | H | i-C$_3$H$_7$ |
| H | 3-CF$_3$ | H | n-C$_4$H$_9$ |
| H | 3-CF$_3$ | H | s-C$_4$H$_9$ |
| H | 3-CF$_3$ | H | t-C$_4$H$_9$ |
| H | 3-CF$_3$ | H | C$_5$H$_{11}$ |
| H | 3-CF$_3$ | H | C$_6$H$_{13}$ |
| H | 3-CF$_3$ | H | Allyl |
| H | 3-CF$_3$ | H | Propargyl |
| H | 3-CF$_3$ | H | Cyclopropyl |
| H | 3-CF$_3$ | H | Cyclobutyl |
| H | 3-CF$_3$ | H | Cyclopentyl |
| H | 3-CF$_3$ | H | Cyclohexyl |
| H | 3-CF$_3$ | H | CF$_3$ |
| H | 3-CF$_3$ | H | CCl$_3$ |
| H | 3-CF$_3$ | H | CH$_2$CF$_3$ |
| H | 3-CF$_3$ | H | CH$_2$CCl$_3$ |
| H | 3-CF$_3$ | H | CH$_2$CH$_2$F |
| H | 3-CF$_3$ | H | CH$_2$CH$_2$Cl |
| H | 3-CF$_3$ | H | CH$_2$CF$_3$ |
| H | 3-CF$_3$ | H | CH$_2$CCl$_3$ |
| H | 3-CF$_3$ | | CH$_2$CH$_2$CH$_2$ |
| H | 3-CF$_3$ | | CH$_2$(CH$_2$)$_2$CH$_2$ |
| H | 3-CF$_3$ | | CH$_2$(CH$_2$)$_3$CH$_2$ |
| H | 3-CF$_3$ | | CH$_2$(CH$_2$)$_4$CH$_2$ |
| H | 3-CF$_3$ | | (CH$_2$)$_2$O(CH$_2$)$_2$ |
| H | 3-CF$_3$ | | (CH$_2$)$_2$S(CH$_2$)$_2$ |
| H | 3-CF$_3$ | | (CH$_2$)$_2$NH(CH$_2$)$_2$ |
| H | 3-CF$_3$ | | (CH$_2$)$_2$NCH$_3$(CH$_2$)$_2$ |
| H | 3-CF$_3$ | H | C$_6$H$_4$ |
| H | 3-CF$_3$ | H | 2-FC$_6$H$_4$ |
| H | 3-CF$_3$ | H | 3-FC$_6$H$_4$ |
| H | 3-CF$_3$ | H | 4-FC$_6$H$_4$ |
| H | 3-CF$_3$ | H | 2-ClC$_6$H$_4$ |
| H | 3-CF$_3$ | H | 3-ClC$_6$H$_4$ |
| H | 3-CF$_3$ | H | 4-ClC$_6$H$_4$ |
| H | 3-CF$_3$ | H | 2,3-F$_2$C$_6$H$_3$ |
| H | 3-CF$_3$ | H | 2,4-F$_2$C$_6$H$_3$ |
| H | 3-CF$_3$ | H | 2,3-Cl$_2$C$_6$H$_3$ |
| H | 3-CF$_3$ | H | 2,4-Cl$_2$C$_6$H$_3$ |
| H | 3-CF$_3$ | H | 2-CH$_3$C$_6$H$_4$ |
| H | 3-CF$_3$ | H | 3-CH$_3$C$_6$H$_4$ |
| H | 3-CF$_3$ | H | 4-CH$_3$C$_6$H$_4$ |
| H | 3-CF$_3$ | H | 2-OCH$_3$C$_6$H$_4$ |
| H | 3-CF$_3$ | H | 3-OCH$_3$C$_6$H$_4$ |
| H | 3-CF$_3$ | H | 4-OCH$_3$C$_6$H$_4$ |
| H | 3-CF$_3$ | H | 2-CF$_3$C$_6$H$_4$ |
| H | 3-CF$_3$ | H | 3-CF$_3$C$_6$H$_4$ |
| H | 3-CF$_3$ | H | 4-CF$_3$C$_6$H$_4$ |
| H | 3-CF$_3$ | H | 2-NO$_2$C$_6$H$_4$ |
| H | 3-CF$_3$ | H | 3-NO$_2$C$_6$H$_4$ |
| H | 3-CF$_3$ | H | 4-NO$_2$C$_6$H$_4$ |
| H | 3-CF$_3$ | H | 2-CNC$_6$H$_4$ |
| H | 3-CF$_3$ | H | 4-CNC$_6$H$_4$ |
| H | 3-CF$_3$ | H | 2-SO$_3$HC$_6$H$_4$ |
| H | 3-CF$_3$ | H | 3-SO$_3$HC$_6$H$_4$ |
| H | 3-CF$_3$ | H | 4-SO$_3$HC$_6$H$_4$ |
| H | 3-CF$_3$ | H | OH |
| H | 3-CF$_3$ | H | OCH$_3$ |
| H | 3-CF$_3$ | H | OC$_2$H$_5$ |
| H | 3-CF$_3$ | H | OC$_4$H$_9$ |

TABLE 1-continued

Structure: Pyrazine with R1/R2-substituted phenoxy group at one position, and C(=O)NR4R5 amide at another position. Z = C=O, X = S, n = 0, R³ = H. Formula I.1

| R¹ | R² | R⁴ | R⁵ |
|---|---|---|---|
| H | 3-CF₃ | H | OC₅H₁₁ |
| H | 3-CF₃ | H | OC₆H₁₃ |
| H | 3-CF₃ | H | OAllyl |
| H | 3-CF₃ | H | OPropargyl |
| H | 3-CF₃ | H | OCF₃ |
| H | 3-CF₃ | H | OCCl₃ |
| H | 3-CF₃ | H | OCH₂CH₂F |
| H | 3-CF₃ | H | OCH₂CH₂Cl |
| H | 3-CF₃ | H | OCH₂CF₃ |
| H | 3-CF₃ | H | OCH₂CCl₃ |
| H | 3-CF₃ | H | OC₆H₄ |
| H | 3-CF₃ | H | O(2-FC₆H₄) |
| H | 3-CF₃ | H | O(3-FC₆H₄) |
| H | 3-CF₃ | H | O(4-FC₆H₄) |
| H | 3-CF₃ | H | O(2-ClC₆H₄) |
| H | 3-CF₃ | H | O(3-ClC₆H₄) |
| H | 3-CF₃ | H | O(4-ClC₆H₄) |
| H | 3-CF₃ | H | O(2,3-F₂C₆H₃) |
| H | 3-CF₃ | H | O(2,4-F₂C₆H₃) |
| H | 3-CF₃ | H | O(2,3-Cl₂C₆H₃) |
| H | 3-CF₃ | H | O(2,4-Cl₂C₆H₃) |
| H | 3-CF₃ | H | O(2-CF₃C₆H₄) |
| H | 3-CF₃ | H | O(3-CF₃C₆H₄) |
| H | 3-CF₃ | H | O(4-CF₃OC₆H₄) |
| H | 3-CF₃ | H | NH₂ |
| H | 3-CF₃ | H | NHCH₃ |
| H | 3-CF₃ | H | NHC₂H₅ |
| H | 3-CF₃ | H | NHC₃H₇ |
| H | 3-CF₃ | H | NHC₄H₉ |
| H | 3-CF₃ | H | NHC₅H₁₁ |
| H | 3-CF₃ | H | NHC₆H₁₃ |
| H | 3-CF₃ | H | NHAllyl |
| H | 3-CF₃ | H | NHPropargyl |
| H | 3-CF₃ | H | NHCF₃ |
| H | 3-CF₃ | H | NHCCl₃ |
| H | 3-CF₃ | H | NHCH₂CH₂F |
| H | 3-CF₃ | H | NHCH₂CH₂Cl |
| H | 3-CF₃ | H | NHCH₂CF₃ |
| H | 3-CF₃ | H | NHCH₂CCl₃ |
| H | 3-CF₃ | H | NHC₆H₄ |
| H | 3-CF₃ | H | NH(2-FC₆H₄) |
| H | 3-CF₃ | H | NH(3-FC₆H₄) |
| H | 3-CF₃ | H | NH(4-C₆H₄) |
| H | 3-CF₃ | H | NH(2-ClC₆H₄) |
| H | 3-CF₃ | H | NH(3-ClC₆H₄) |
| H | 3-CF₃ | H | NH(4-ClC₆H₄) |
| H | 3-CF₃ | H | NH(2,3-F₂C₆H₃) |
| H | 3-CF₃ | H | NH(2,4-F₂C₆H₃) |
| H | 3-CF₃ | H | NH(2,3-Cl₂C₆H₃) |
| H | 3-CF₃ | H | NH(2,4-Cl₂C₆H₃) |
| H | 3-CF₃ | H | NH(2-CF₃C₆H₄) |
| H | 3-CF₃ | H | NH(3-CF₃C₆H₄) |
| H | 3-CF₃ | H | NH(4-CF₃C₆H₄) |
| H | 3-CF₃ | H | (CH₂)₂OH |
| H | 3-CF₃ | H | (CH₂)₂OCH₃ |
| H | 3-CF₃ | H | (CH₂)₂CO₂H |
| H | 3-CF₃ | H | (CH₂)₂CO₂CH₃ |
| H | 3-CF₃ | H | (CH₂)₂CN |
| H | 3-CF₃ | H | (CH₂)₂NH₂ |
| H | 3-CF₃ | H | (CH₂)₂NHCH₃ |
| H | 3-CF₃ | H | (CH₂)₂N(CH₃)₂ |
| H | 3-CF₃ | H | Gly—OtBu |
| H | 3-CF₃ | H | Gly |
| H | 3-CF₃ | H | Ala—OtBu |
| H | 3-CF₃ | H | Ala |
| H | 3-CF₃ | H | Val—OtBu |
| H | 3-CF₃ | H | Val |
| H | 3-CF₃ | H | Phe—OtBu |
| H | 3-CF₃ | H | Phe |
| H | 3-CF₃ | H | Pro—OtBu |
| H | 3-CF₃ | H | Pro |
| H | 3-CF₃ | H | Ser |
| H | 3-CF₃ | H | Cys |
| H | 3-CF₃ | H | Asp |
| H | 3-CF₃ | H | Tyr |
| H | 3-CF₃ | H | Try |
| H | 3-CF₃ | CH₃ | CH₃ |
| H | 3-CF₃ | CH₃ | C₂H₅ |
| H | 3-CF₃ | CH₃ | n-C₃H₇ |
| H | 3-CF₃ | CH₃ | i-C₃H₇ |
| H | 3-CF₃ | CH₃ | n-C₄H₉ |
| H | 3-CF₃ | CH₃ | s-C₄H₉ |
| H | 3-CF₃ | CH₃ | t-C₄H₉ |
| H | 3-CF₃ | CH₃ | C₅H₁₁ |
| H | 3-CF₃ | CH₃ | C₆H₁₃ |
| H | 3-CF₃ | CH₃ | Allyl |
| H | 3-CF₃ | CH₃ | Propargyl |
| H | 3-CF₃ | CH₃ | Cyclopropyl |
| H | 3-CF₃ | CH₃ | Cyclobutyl |
| H | 3-CF₃ | CH₃ | Cyclopentyl |
| H | 3-CF₃ | CH₃ | Cyclohexyl |
| H | 3-CF₃ | CH₃ | CF₃ |
| H | 3-CF₃ | CH₃ | CCl₃ |
| H | 3-CF₃ | CH₃ | CH₂CF₃ |
| H | 3-CF₃ | CH₃ | CH₂CCl₃ |
| H | 3-CF₃ | CH₃ | CH₂CH₂F |
| H | 3-CF₃ | CH₃ | CH₂CH₂Cl |
| H | 3-CF₃ | CH₃ | CH₂CF₃ |
| H | 3-CF₃ | CH₃ | CH₂CCl₃ |
| H | 3-CF₃ | CH₃ | C₆H₄ |
| H | 3-CF₃ | CH₃ | 2-FC₆H₄ |
| H | 3-CF₃ | CH₃ | 3-FC₆H₄ |
| H | 3-CF₃ | CH₃ | 4-FC₆H₄ |
| H | 3-CF₃ | CH₃ | 2-ClC₆H₄ |
| H | 3-CF₃ | CH₃ | 3-ClC₆H₄ |
| H | 3-CF₃ | CH₃ | 4-ClC₆H₄ |
| H | 3-CF₃ | CH₃ | 2,3-F₂C₆H₃ |
| H | 3-CF₃ | CH₃ | 2,4-F₂C₆H₃ |
| H | 3-CF₃ | CH₃ | 2,3-Cl₂C₆H₃ |
| H | 3-CF₃ | CH₃ | 2,4-Cl₂C₆H₃ |
| H | 3-CF₃ | CH₃ | 2-CH₃C₆H₄ |
| H | 3-CF₃ | CH₃ | 3-CH₃C₆H₄ |
| H | 3-CF₃ | CH₃ | 4-CH₃C₆H₄ |
| H | 3-CF₃ | CH₃ | 2-OCH₃C₆H₄ |
| H | 3-CF₃ | CH₃ | 3-OCH₃C₆H₄ |
| H | 3-CF₃ | CH₃ | 4-OCH₃C₆H₄ |
| H | 3-CF₃ | CH₃ | 2-CF₃C₆H₄ |
| H | 3-CF₃ | CH₃ | 3-CF₃C₆H₄ |
| H | 3-CF₃ | CH₃ | 4-CF₃C₆H₄ |
| H | 3-CF₃ | CH₃ | 2-NO₂C₆H₄ |
| H | 3-CF₃ | CH₃ | 3-NO₂C₆H₄ |
| H | 3-CF₃ | CH₃ | 4-NO₂C₆H₄ |
| H | 3-CF₃ | CH₃ | 2-CNC₆H₄ |
| H | 3-CF₃ | CH₃ | 3-CNC₆H₄ |
| H | 3-CF₃ | CH₃ | 4-CNC₆H₄ |
| H | 3-CF₃ | CH₃ | 2-SO₃HC₆H₄ |
| H | 3-CF₃ | CH₃ | 3-SO₃HC₆H₄ |
| H | 3-CF₃ | CH₃ | 4-SO₃HC₆H₄ |
| H | 3-CF₃ | CH₃ | OH |
| H | 3-CF₃ | CH₃ | OCH₃ |
| H | 3-CF₃ | CH₃ | OC₂H₅ |
| H | 3-CF₃ | CH₃ | OC₃H₇ |
| H | 3-CF₃ | CH₃ | OC₄H₉ |
| H | 3-CF₃ | CH₃ | OC₅H₁₁ |

TABLE 1-continued

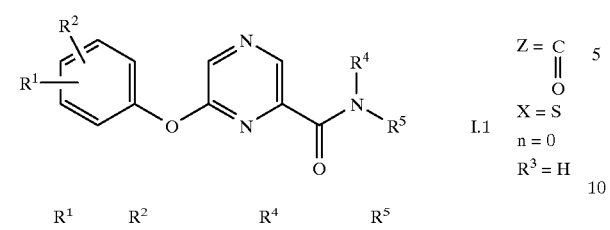

Z = C=O, X = S, n = 0, R³ = H  I.1

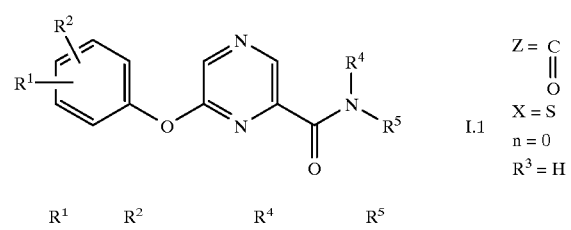

Z = C=O, X = S, n = 0, R³ = H  I.1

| R¹ | R² | R⁴ | R⁵ | R¹ | R² | R⁴ | R⁵ |
|---|---|---|---|---|---|---|---|
| H | 3-CF₃ | CH₃ | OC₅H₁₃ | H | 3-CF₃ | CH₃ | Phe |
| H | 3-CF₃ | CH₃ | OAllyl | H | 3-CF₃ | CH₃ | Pro—OtBu |
| H | 3-CF₃ | CH₃ | OPropargyl | H | 3-CF₃ | CH₃ | Pro |
| H | 3-CF₃ | CH₃ | OCF₃ | H | 3-CF₃ | CH₃ | Ser |
| H | 3-CF₃ | CH₃ | OCCl₃ | H | 3-CF₃ | CH₃ | Cys |
| H | 3-CF₃ | CH₃ | OCH₂CH₂F | H | 3-CF₃ | CH₃ | Asp |
| H | 3-CF₃ | CH₃ | OCH₂CH₂Cl | H | 3-CF₃ | CH₃ | Tyr |
| H | 3-CF₃ | CH₃ | OCH₂CF₃ | H | 3-CF₃ | CH₃ | Try |
| H | 3-CF₃ | CH₃ | OCH₂CCl₃ | 2-F | 4-F | H | CH₃ |
| H | 3-CF₃ | CH₃ | OC₆H₄ | 2-F | 4-F | H | C₂H₅ |
| H | 3-CF₃ | CH₃ | O(2-FC₆H₄) | 2-F | 4-F | H | n-C₃H₇ |
| H | 3-CF₃ | CH₃ | O(3-FC₆H₄) | 2-F | 4-F | H | i-C₃H₇ |
| H | 3-CF₃ | CH₃ | O(4-FC₆H₄) | 2-F | 4-F | H | n-C₄H₇ |
| H | 3-CF₃ | CH₃ | O(2-ClC₆H₄) | 2-F | 4-F | H | s-C₄H₉ |
| H | 3-CF₃ | CH₃ | O(3-ClC₆H₄) | 2-F | 4-F | H | t-C₄H₉ |
| H | 3-CF₃ | CH₃ | O(4-ClC₆H₄) | 2-F | 4-F | H | C₅H₁₁ |
| H | 3-CF₃ | CH₃ | O(2,3-F₂O₆H₃) | 2-F | 4-F | H | C₆H₁₃ |
| H | 3-CF₃ | CH₃ | O(2,4-F₂C₆H₃) | 2-F | 4-F | H | Allyl |
| H | 3-CF₃ | CH₃ | O(2,3-Cl₂C₆H₃) | 2-F | 4-F | H | Propargyl |
| H | 3-CF₃ | CH₃ | O(2,4-Cl₂C₆H₃) | 2-F | 4-F | H | Cyclopropyl |
| H | 3-CF₃ | CH₃ | O(2-CF₃C₆H₄) | 2-F | 4-F | H | Cyclobutyl |
| H | 3-CF₃ | CH₃ | O(3-CF₃C₆H₄) | 2-F | 4-F | H | Cyclopentyl |
| H | 3-CF₃ | CH₃ | O(4-CF₃C₆H₄) | 2-F | 4-F | H | Cyclohexyl |
| H | 3-CF₃ | CH₃ | NH₂ | 2-F | 4-F | H | CF₃ |
| H | 3-CF₃ | CH₃ | NHCH₃ | 2-F | 4-F | H | CCl₃ |
| H | 3-CF₃ | CH₃ | NHC₂H₅ | 2-F | 4-F | H | CH₂CF₃ |
| H | 3-CF₃ | CH₃ | NHC₃H₇ | 2-F | 4-F | H | CH₂CCl₃ |
| H | 3-CF₃ | CH₃ | NHC₄H₉ | 2-F | 4-F | H | CH₂CH₂F |
| H | 3-CF₃ | CH₃ | NHC₅H₁₁ | 2-F | 4-F | H | CH₂CH₂Cl |
| H | 3-CF₃ | CH₃ | NHC₆H₁₃ | 2-F | 4-F | H | CH₂CF₃ |
| H | 3-CF₃ | CH₃ | NHAllyl | 2-F | 4-F | H | CH₂CCl₃ |
| H | 3-CF₃ | CH₃ | NHPropargyl | 2-F | 4-F | | CH₂CH₂CH₂ |
| H | 3-CF₃ | CH₃ | NHCF₃ | 2-F | 4-F | | CH₂(CH₂)₂CH₂ |
| H | 3-CF₃ | CH₃ | NHCCl₃ | 2-F | 4-F | | CH₂(CH₂)₃CH₂ |
| H | 3-CF₃ | CH₃ | NHCH₂CH₂F | 2-F | 4-F | | CH₂(CH₂)₄CH₂ |
| H | 3-CF₃ | CH₃ | NHCH₂CH₂Cl | 2-F | 4-F | | (CH₂)₂O(CH₂)₂ |
| H | 3-CF₃ | CH₃ | NHCH₂CF₃ | 2-F | 4-F | | (CH₂)₂S(CH₂)₂ |
| H | 3-CF₃ | CH₃ | NHCH₂CCl₃ | 2-F | 4-F | | (CH₂)₂NH(CH₂)₂ |
| H | 3-CF₃ | CH₃ | NHC₆H₄ | 2-F | 4-F | | (CH₂)₂NCH₃(CH₂)₂ |
| H | 3-CF₃ | CH₃ | NH(2-FC₆H₄) | 2-F | 4-F | H | C₆H₄ |
| H | 3-CF₃ | CH₃ | NH(3-FC₆H₄) | 2-F | 4-F | H | 2-FC₆H₄ |
| H | 3-CF₃ | CH₃ | NH(4-C₆H₄) | 2-F | 4-F | H | 3-FC₆H₄ |
| H | 3-CF₃ | CH₃ | NH(2-ClC₆H₄) | 2-F | 4-F | H | 4-FC₆H₄ |
| H | 3-CF₃ | CH₃ | NH(3-ClC₆H₄) | 2-F | 4-F | H | 2-ClC₆H₄ |
| H | 3-CF₃ | CH₃ | NH(4-ClC₆H₄) | 2-F | 4-F | H | 3-ClC₆H₄ |
| H | 3-CF₃ | CH₃ | NH(2,3-F₂C₆H₃) | 2-F | 4-F | H | 4-ClC₆H₄ |
| H | 3-CF₃ | CH₃ | NH(2,4-F₂C₆H₃) | 2-F | 4-F | H | 2,3-F₂C₆H₃ |
| H | 3-CF₃ | CH₃ | NH(2,3-Cl₂C₆H₃) | 2-F | 4-F | H | 2,4-F₂C₆H₃ |
| H | 3-CF₃ | CH₃ | NH(2,4-Cl₂C₆H₃) | 2-F | 4-F | H | 2,3-Cl₂C₆H₃ |
| H | 3-CF₃ | CH₃ | NH(2-CF₃C₆H₄) | 2-F | 4-F | H | 2,4-Cl₂C₆H₃ |
| H | 3-CF₃ | CH₃ | NH(3-CF₃C₆H₄) | 2-F | 4-F | H | 2-CH₃C₆H₄ |
| H | 3-CF₃ | CH₃ | NH(4-CF₃C₆H₄) | 2-F | 4-F | H | 3-CH₃C₆H₄ |
| H | 3-CF₃ | CH₃ | (CH₂)₂OH | 2-F | 4-F | H | 4-CH₃C₆H₄ |
| H | 3-CF₃ | CH₃ | (CH₂)₂OCH₃ | 2-F | 4-F | H | 2-OCH₃C₆H₄ |
| H | 3-CF₃ | CH₃ | (CH₂)₂CO₂H | 2-F | 4-F | H | 3-OCH₃C₆H₄ |
| H | 3-CF₃ | CH₃ | (CH₂)₂CO₂CH₃ | 2-F | 4-F | H | 4-OCH₃C₆H₄ |
| H | 3-CF₃ | CH₃ | (CH₂)₂CN | 2-F | 4-F | H | 2-CF₃C₆H₄ |
| H | 3-CF₃ | CH₃ | (CH₂)₂NH₂ | 2-F | 4-F | H | 3-CF₃C₆H₄ |
| H | 3-CF₃ | CH₃ | (CH₂)₂NHCH₃ | 2-F | 4-F | H | 4-CF₃C₆H₄ |
| H | 3-CF₃ | CH₃ | (CH₂)₂N(CH₃)₂ | 2-F | 4-F | H | 2-NO₂C₆H₄ |
| H | 3-CF₃ | CH₃ | Gly—OtBu | 2-F | 4-F | H | 3-NO₂C₆H₄ |
| H | 3-CF₃ | CH₃ | Gly | 2-F | 4-F | H | 4-NO₂C₆H₄ |
| H | 3-CF₃ | CH₃ | Ala—OtBu | 2-F | 4-F | H | 2-CNC₆H₄ |
| H | 3-CF₃ | CH₃ | Ala | 2-F | 4-F | H | 3-CNC₆H₄ |
| H | 3-CF₃ | CH₃ | Val—OtBu | 2-F | 4-F | H | 4-CNC₆H₄ |
| H | 3-CF₃ | CH₃ | Val | 2-F | 4-F | H | 2-SO₃HC₆H₄ |
| H | 3-CF₃ | CH₃ | Phe—OtBu | 2-F | 4-F | H | 3-SO₃HC₆H₄ |

TABLE 1-continued

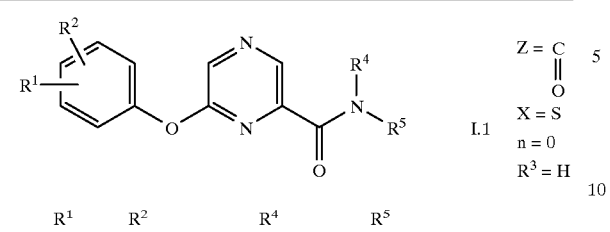

Z = C=O
X = S
n = 0
R³ = H
I.1

| R¹ | R² | R⁴ | R⁵ |
|---|---|---|---|
| 2-F | 4-F | H | 4-SO₃HC₆H₄ |
| 2-F | 4-F | H | OH |
| 2-F | 4-F | H | OCH₃ |
| 2-F | 4-F | H | OC₂H₅ |
| 2-F | 4-F | H | OC₃H₇ |
| 2-F | 4-F | H | OC₄H₉ |
| 2-F | 4-F | H | OC₅H₁₁ |
| 2-F | 4-F | H | OC₆H₁₃ |
| 2-F | 4-F | H | OAllyl |
| 2-F | 4-F | H | OPropargyl |
| 2-F | 4-F | H | OCF₃ |
| 2-F | 4-F | H | OCCl₃ |
| 2-F | 4-F | H | OCH₂CH₂F |
| 2-F | 4-F | H | OCH₂CH₂Cl |
| 2-F | 4-F | H | OCH₂CF₃ |
| 2-F | 4-F | H | OCH₂CCl₃ |
| 2-F | 4-F | H | OC₆H₄ |
| 2-F | 4-F | H | O(2-FC₆H₄) |
| 2-F | 4-F | H | O(3-FC₆H₄) |
| 2-F | 4-F | H | O(4-FC₆H₄) |
| 2-F | 4-F | H | O(2-ClC₆H₄) |
| 2-F | 4-F | H | O(3-ClC₆H₄) |
| 2-F | 4-F | H | O(4-ClC₆H₄) |
| 2-F | 4-F | H | O(2,3-F₂C₆H₃) |
| 2-F | 4-F | H | O(2,4-F₂C₆H₃) |
| 2-F | 4-F | H | O(2,3-Cl₂C₆H₃) |
| 2-F | 4-F | H | O(2,4-Cl₂C₆H₃) |
| 2-F | 4-F | H | O(2-CF₃C₆H₄) |
| 2-F | 4-F | H | O(3-CF₃C₆H₄) |
| 2-F | 4-F | H | O(4-CF₃C₆H₄) |
| 2-F | 4-F | H | NH₂ |
| 2-F | 4-F | H | NHCH₃ |
| 2-F | 4-F | H | NHC₂H₅ |
| 2-F | 4-F | H | NHC₃H₇ |
| 2-F | 4-F | H | NHC₄H₉ |
| 2-F | 4-F | H | NHC₅H₁₁ |
| 2-F | 4-F | H | NHC₆H₁₃ |
| 2-F | 4-F | H | NHAllyl |
| 2-F | 4-F | H | NHPropargyl |
| 2-F | 4-F | H | NHCF₃ |
| 2-F | 4-F | H | NHCCl₃ |
| 2-F | 4-F | H | NHCH₂CH₂F |
| 2-F | 4-F | H | NHCH₂CH₂Cl |
| 2-F | 4-F | H | NHCH₂CF₃ |
| 2-F | 4-F | H | NHCH₂CCl₃ |
| 2-F | 4-F | H | NHC₆H₄ |
| 2-F | 4-F | H | NH(2-FC₆H₄) |
| 2-F | 4-F | H | NH(3-FC₆H₄) |
| 2-F | 4-F | H | NH(4-C₆H₄) |
| 2-F | 4-F | H | NH(2-ClC₆H₄) |
| 2-F | 4-F | H | NH(3-ClC₆H₄) |
| 2-F | 4-F | H | NH(4-ClC₆H₄) |
| 2-F | 4-F | H | NH(2,3-F₂C₆H₃) |
| 2-F | 4-F | H | NH(2,4-F₂C₆H₃) |
| 2-F | 4-F | H | NH(2,3-Cl₂C₆H₃) |
| 2-F | 4-F | H | NH(2,4-Cl₂C₆H₃) |
| 2-F | 4-F | H | NH(2-CF₃C₆H₄) |
| 2-F | 4-F | H | NH(3-CF₃C₆H₄) |
| 2-F | 4-F | H | NH(4-CF₃C₆H₄) |
| 2-F | 4-F | H | (CH₂)₂OH |
| 2-F | 4-F | H | (CH₂)₂OCH₃ |
| 2-F | 4-F | H | (CH₂)₂CO₂H |
| 2-F | 4-F | H | (CH₂)₂CO₂CH₃ |
| 2-F | 4-F | H | (CH₂)₂CN |
| 2-F | 4-F | H | (CH₂)₂NH₂ |
| 2-F | 4-F | H | (CH₂)₂NHCH₃ |
| 2-F | 4-F | H | (CH₂)₂N(CH₃)₂ |

TABLE 1-continued

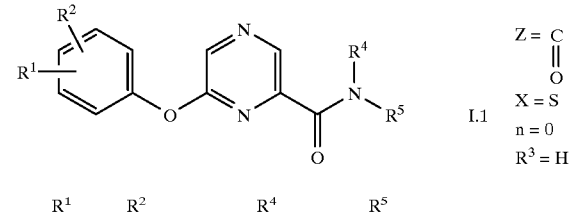

Z = C=O
X = S
n = 0
R³ = H
I.1

| R¹ | R² | R⁴ | R⁵ |
|---|---|---|---|
| 2-F | 4-F | H | Gly—OtBu |
| 2-F | 4-F | H | Gly |
| 2-F | 4-F | H | Ala—OtBu |
| 2-F | 4-F | H | Ala |
| 2-F | 4-F | H | Val—OtBu |
| 2-F | 4-F | H | Val |
| 2-F | 4-F | H | Phe—OtBu |
| 2-F | 4-F | H | Phe |
| 2-F | 4-F | H | Pro—OtBu |
| 2-F | 4-F | H | Pro |
| 2-F | 4-F | H | Ser |
| 2-F | 4-F | H | Cys |
| 2-F | 4-F | H | Asp |
| 2-F | 4-F | H | Tyr |
| 2-F | 4-F | H | Try |
| 2-F | 4-F | CH₃ | CH₃ |
| 2-F | 4-F | CH₃ | C₂H₅ |
| 2-F | 4-F | CH₃ | n-C₃H₇ |
| 2-F | 4-F | CH₃ | i-C₃H₇ |
| 2-F | 4-F | CH₃ | n-C₄H₉ |
| 2-F | 4-F | CH₃ | s-C₄H₉ |
| 2-F | 4-F | CH₃ | t-C₄H₉ |
| 2-F | 4-F | CH₃ | C₅H₁₁ |
| 2-F | 4-F | CH₃ | C₆H₁₃ |
| 2-F | 4-F | CH₃ | Allyl |
| 2-F | 4-F | CH₃ | Propargyl |
| 2-F | 4-F | CH₃ | Cyclopropyl |
| 2-F | 4-F | CH₃ | Cyclobutyl |
| 2-F | 4-F | CH₃ | Cyclopentyl |
| 2-F | 4-F | CH₃ | Cyclohexyl |
| 2-F | 4-F | CH₃ | CF₃ |
| 2-F | 4-F | CH₃ | CCl₃ |
| 2-F | 4-F | CH₃ | CH₂CF₃ |
| 2-F | 4-F | CH₃ | CH₂CCl₃ |
| 2-F | 4-F | CH₃ | CH₂CH₂F |
| 2-F | 4-F | CH₃ | CH₂CH₂Cl |
| 2-F | 4-F | CH₃ | CH₂CF₃ |
| 2-F | 4-F | CH₃ | CH₂CCl₃ |
| 2-F | 4-F | CH₃ | C₆H₄ |
| 2-F | 4-F | CH₃ | 2-FC₆H₄ |
| 2-F | 4-F | CH₃ | 3-FC₆H₄ |
| 2-F | 4-F | CH₃ | 4-FC₆H₄ |
| 2-F | 4-F | CH₃ | 2-ClC₆H₄ |
| 2-F | 4-F | CH₃ | 3-ClC₆H₄ |
| 2-F | 4-F | CH₃ | 4-ClC₆H₄ |
| 2-F | 4-F | CH₃ | 2,3-F₂C₆H₃ |
| 2-F | 4-F | CH₃ | 2,4-F₂C₆H₃ |
| 2-F | 4-F | CH₃ | 2,3-Cl₂C₆H₃ |
| 2-F | 4-F | CH₃ | 2,4-Cl₂C₆H₃ |
| 2-F | 4-F | CH₃ | 2-CH₃C₆H₄ |
| 2-F | 4-F | CH₃ | 3-CH₃C₆H₄ |
| 2-F | 4-F | CH₃ | 4-CH₃C₆H₄ |
| 2-F | 4-F | CH₃ | 2-OCH₃C₆H₄ |
| 2-F | 4-F | CH₃ | 3-OCH₃C₆H₄ |
| 2-F | 4-F | CH₃ | 4-OCH₃C₆H₄ |
| 2-F | 4-F | CH₃ | 2-CF₃C₆H₄ |
| 2-F | 4-F | CH₃ | 3-CF₃C₆H₄ |
| 2-F | 4-F | CH₃ | 4-CF₃C₆H₄ |
| 2-F | 4-F | CH₃ | 2-NO₂C₆H₄ |
| 2-F | 4-F | CH₃ | 3-NO₂C₆H₄ |
| 2-F | 4-F | CH₃ | 4-NO₂C₆H₄ |
| 2-F | 4-F | CH₃ | 2-CNC₆H₄ |
| 2-F | 4-F | CH₃ | 3-CNC₆H₄ |
| 2-F | 4-F | CH₃ | 4-CNC₆H₄ |
| 2-F | 4-F | CH₃ | 2-SO₃HC₆H₄ |
| 2-F | 4-F | CH₃ | 3-SO₃HC₆H₄ |
| 2-F | 4-F | CH₃ | 4-SO₃HC₆H₄ |

TABLE 1-continued

Structure I.1: Pyrazine carboxamide with aryloxy substituent; Z = C(=O), X = S, n = 0, R³ = H

| R¹ | R² | R⁴ | R⁵ |
|---|---|---|---|
| 2-F | 4-F | CH₃ | OH |
| 2-F | 4-F | CH₃ | OCH₃ |
| 2-F | 4-F | CH₃ | OC₂H₅ |
| 2-F | 4-F | CH₃ | OC₃H₇ |
| 2-F | 4-F | CH₃ | OC₄H₉ |
| 2-F | 4-F | CH₃ | OC₅H₁₁ |
| 2-F | 4-F | CH₃ | OC₆H₁₃ |
| 2-F | 4-F | CH₃ | OAllyl |
| 2-F | 4-F | CH₃ | OPropargyl |
| 2-F | 4-F | CH₃ | OCF₃ |
| 2-F | 4-F | CH₃ | OCCl₃ |
| 2-F | 4-F | CH₃ | OCH₂CH₂F |
| 2-F | 4-F | CH₃ | OCH₂CH₂Cl |
| 2-F | 4-F | CH₃ | OCH₂CF₃ |
| 2-F | 4-F | CH₃ | OCH₂CCl₃ |
| 2-F | 4-F | CH₃ | OC₆H₄ |
| 2-F | 4-F | CH₃ | O(2-FC₆H₄) |
| 2-F | 4-F | CH₃ | O(3-FC₆H₄) |
| 2-F | 4-F | CH₃ | O(4-FC₆H₄) |
| 2-F | 4-F | CH₃ | O(2-ClC₆H₄) |
| 2-F | 4-F | CH₃ | O(3-ClC₆H₄) |
| 2-F | 4-F | CH₃ | O(4-ClC₆H₄) |
| 2-F | 4-F | CH₃ | O(2,3-F₂C₆H₃) |
| 2-F | 4-F | CH₃ | O(2,4-F₂C₆H₃) |
| 2-F | 4-F | CH₃ | O(2,3-Cl₂C₆H₃) |
| 2-F | 4-F | CH₃ | O(2,4-Cl₂C₆H₃) |
| 2-F | 4-F | CH₃ | O(2-CF₃C₆H₄) |
| 2-F | 4-F | CH₃ | O(3-CF₃C₆H₄) |
| 2-F | 4-F | CH₃ | O(4-CF₃C₆H₄) |
| 2-F | 4-F | CH₃ | NH₂ |
| 2-F | 4-F | CH₃ | NHCH₃ |
| 2-F | 4-F | CH₃ | NHC₂H₅ |
| 2-F | 4-F | CH₃ | NHC₃H₇ |
| 2-F | 4-F | CH₃ | NHC₄H₉ |
| 2-F | 4-F | CH₃ | NHC₅H₁₁ |
| 2-F | 4-F | CH₃ | NHC₆H₁₃ |
| 2-F | 4-F | CH₃ | NHAllyl |
| 2-F | 4-F | CH₃ | NHPropargyl |
| 2-F | 4-F | CH₃ | NHCF₃ |
| 2-F | 4-F | CH₃ | NHCCl₃ |
| 2-F | 4-F | CH₃ | NHCH₂CH₂F |
| 2-F | 4-F | CH₃ | NHCH₂CH₂Cl |
| 2-F | 4-F | CH₃ | NHCH₂CF₃ |
| 2-F | 4-F | CH₃ | NHCH₂CCl₃ |
| 2-F | 4-F | CH₃ | NHC₆H₄ |
| 2-F | 4-F | CH₃ | NH(2-FC₆H₄) |
| 2-F | 4-F | CH₃ | NH(3-FC₆H₄) |
| 2-F | 4-F | CH₃ | NH(4-C₆H₄) |
| 2-F | 4-F | CH₃ | NH(2-ClC₆H₄) |
| 2-F | 4-F | CH₃ | NH(3-ClC₆H₄) |
| 2-F | 4-F | CH₃ | NH(4-ClC₆H₄) |
| 2-F | 4-F | CH₃ | NH(2,3-F₂C₆H₃) |
| 2-F | 4-F | CH₃ | NH(2,4-F₂C₆H₃) |
| 2-F | 4-F | CH₃ | NH(2,3-Cl₂C₆H₃) |
| 2-F | 4-F | CH₃ | NH(2,4-Cl₂C₆H₃) |
| 2-F | 4-F | CH₃ | NH(2-CF₃C₆H₄) |
| 2-F | 4-F | CH₃ | NH(3-CF₃C₆H₄) |
| 2-F | 4-F | CH₃ | NH(4-CF₃C₆H₄) |
| 2-F | 4-F | CH₃ | (CH₂)₂OH |
| 2-F | 4-F | CH₃ | (CH₂)₂OCH₃ |
| 2-F | 4-F | CH₃ | (CH₂)₂CO₂H |
| 2-F | 4-F | CH₃ | (CH₂)₂CO₂CH₃ |
| 2-F | 4-F | CH₃ | (CH₂)₂CN |
| 2-F | 4-F | CH₃ | (CH₂)₂NH₂ |
| 2-F | 4-F | CH₃ | (CH₂)₂NHCH₃ |
| 2-F | 4-F | CH₃ | (CH₂)₂N(CH₃)₂ |
| 2-F | 4-F | CH₃ | Gly—OtBu |
| 2-F | 4-F | CH₃ | Gly |
| 2-F | 4-F | CH₃ | Ala—OtBu |
| 2-F | 4-F | CH₃ | Ala |
| 2-F | 4-F | CH₃ | Val—OtBu |
| 2-F | 4-F | CH₃ | Val |
| 2-F | 4-F | CH₃ | Phe—OtBu |
| 2-F | 4-F | CH₃ | Phe |
| 2-F | 4-F | CH₃ | Pro—OtBu |
| 2-F | 4-F | CH₃ | Pro |
| 2-F | 4-F | CH₃ | Ser |
| 2-F | 4-F | CH₃ | Cys |
| 2-F | 4-F | CH₃ | Asp |
| 2-F | 4-F | CH₃ | Tyr |
| 2-F | 4-F | CH₃ | Try |

TABLE 2

Formula I.3: Z = C(=O), X = OCH₂, n = 1, R³ = H

Compounds of the formula I.3 in which the combination of radicals R¹, R², R⁴ and R⁵ corresponds in each case to a line of the above Table 1 (eg. R¹=H, R²=3-CF₃, R⁴=H and R⁵=CH₃, etc.).

TABLE 3

Formula I.4: Z = C(=S), X = S, n = 0, R³ = H

Compounds of the formula I.4 in which the combination of radicals R¹, R², R⁴ and R⁵ corresponds in each case to a line of the above Table 1 (eg. R¹=H, R²=3-CF₃, R⁴=H and R⁵=CH₃, etc.).

TABLE 4

Formula I.6: Z = C(=O), X = SO₂, n = 0, R³ = H

Compounds of the formula I.6 in which the combination of radicals $R^1$, $R^2$, $R^4$ and $R^5$ corresponds in each case to a line of the above Table 1 (eg. $R^1$=H. $R^2$=3-$CF_3$, $R^4$=H and $R^5$=$CH_3$, etc.).

TABLE 5

I.7

$Z = C{=}S$
$X = SO_2$
$n = 0$
$R^3 = H$

Compounds of the formula I.7 in which the combination of radicals $R^1$, $R^2$, $R^4$ and $R^5$ corresponds in each case to a line of the above Table 1 (eg. $R^1$=H, $R^2$=3-$CF_3$, $R^4$=H and $R^5$=$CH_3$ etc.).

TABLE 6

I.8

| $R^1$ | $R^2$ | p | Y | X |
|---|---|---|---|---|
| H | 3-$CF_3$ | 2 | O | O |
| H | 3-$CF_3$ | 3 | O | O |
| 2-F | 4-F | 2 | O | O |
| 2-F | 4-F | 3 | O | O |
| H | 3-$CF_3$ | 2 | S | O |
| H | 3-$CF_3$ | 3 | S | O |
| 2-F | 4-F | 2 | S | O |
| 2-F | 4-F | 3 | S | O |
| H | 3-$CF_3$ | 2 | O | S |
| H | 3-$CF_3$ | 3 | O | S |
| 2-F | 4-F | 2 | O | S |
| 2-F | 4-F | 3 | O | S |
| H | 3-$CF_3$ | 2 | S | S |
| H | 3-$CF_3$ | 3 | S | S |
| 2-F | 4-F | 2 | S | S |
| 2-F | 4-F | 3 | S | S |

TABLE 7

I.9

| $R^1$ | $R^2$ | Y | X |
|---|---|---|---|
| H | 3-$CF_3$ | O | O |
| H | 3-$CF_3$ | O | O |
| 2-F | 4-F | O | O |
| 2-F | 4-F | O | O |
| H | 3-$CF_3$ | S | O |
| H | 3-$CF_3$ | S | O |
| 2-F | 4-F | S | O |
| 2-F | 4-F | S | O |
| H | 3-$CF_3$ | O | S |

TABLE 7-continued

I.9

| $R^1$ | $R^2$ | Y | X |
|---|---|---|---|
| H | 3-$CF_3$ | O | S |
| 2-F | 4-F | O | S |
| 2-F | 4-F | O | S |
| H | 3-$CF_3$ | S | S |
| H | 3-$CF_3$ | S | S |
| 2-F | 4-F | S | S |
| 2-F | 4-F | S | S |

I.10

$Z = C{=}O$
$X = O$
$n = 0$
$R^3 = H$

| $R^1$ | $R^2$ | $R^4$ | $R^5$ |
|---|---|---|---|
| H | 3-$CF_3$ | H | $CH_3$ |
| H | 3-$CF_3$ | H | $C_2H_5$ |
| H | 3-$CF_3$ | H | n-$C_3H_7$ |
| H | 3-$CF_3$ | H | i-$C_3H_7$ |
| H | 3-$CF_3$ | H | n-$C_4H_9$ |
| H | 3-$CF_3$ | H | s-$C_4H_9$ |
| H | 3-$CF_3$ | H | t-$C_4H_9$ |
| H | 3-$CF_3$ | H | $C_5H_{11}$ |
| H | 3-$CF_3$ | H | $C_6H_{13}$ |
| H | 3-$CF_3$ | H | Allyl |
| H | 3-$CF_3$ | H | Propargyl |
| H | 3-$CF_3$ | H | Cyclopropyl |
| H | 3-$CF_3$ | H | Cyclobutyl |
| H | 3-$CF_3$ | H | Cyclopentyl |
| H | 3-$CF_3$ | H | Cyclohexyl |
| H | 3-$CF_3$ | H | $CF_3$ |
| H | 3-$CF_3$ | H | $CCl_3$ |
| H | 3-$CF_3$ | H | $CH_2CF_3$ |
| H | 3-$CF_3$ | H | $CH_2CCl_3$ |
| H | 3-$CF_3$ | H | $CH_2CH_2F$ |
| H | 3-$CF_3$ | H | $CH_2CH_2Cl$ |
| H | 3-$CF_3$ | H | $CH_2CF_3$ |
| H | 3-$CF_3$ | H | $CH_2CCl_3$ |
| H | 3-$CF_3$ |  | $CH_2CH_2CH_2$ |
| H | 3-$CF_3$ |  | $CH_2(CH_2)_2CH_2$ |
| H | 3-$CF_3$ |  | $CH_2(CH_2)_3CH_2$ |
| H | 3-$CF_3$ |  | $CH_2(CH_2)_4CH_2$ |
| H | 3-$CF_3$ |  | $(CH_2)_2O(CH_2)_2$ |
| H | 3-$CF_3$ |  | $(CH_2)_2S(CH_2)_2$ |
| H | 3-$CF_3$ |  | $(CH_2)_2NH(CH_2)_2$ |
| H | 3-$CF_3$ |  | $(CH_2)_2NCH_3(CH_2)_2$ |
| H | 3-$CF_3$ | H | $C_6H_4$ |
| H | 3-$CF_3$ | H | 2-$FC_6H_4$ |
| H | 3-$CF_3$ | H | 3-$FC_6H_4$ |
| H | 3-$CF_3$ | H | 4-$FC_6H_4$ |
| H | 3-$CF_3$ | H | 2-$ClC_6H_4$ |
| H | 3-$CF_3$ | H | 3-$ClC_6H_4$ |
| H | 3-$CF_3$ | H | 4-$ClC_6H_4$ |
| H | 3-$CF_3$ | H | 2,3-$F_2C_6H_3$ |

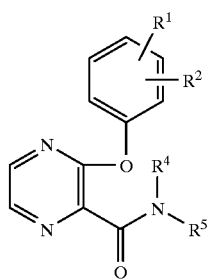

Z = C
    ‖
    O
X = O
n = 0
R³ = H

I.10

| R¹ | R² | R⁴ | R⁵ |
|---|---|---|---|
| H | 3-CF₃ | H | 2,4-F₂C₆H₃ |
| H | 3-CF₃ | H | 2,3-Cl₂C₆H₃ |
| H | 3-CF₃ | H | 2,4-Cl₂C₆H₃ |
| H | 3-CF₃ | H | 2-CH₃C₆H₄ |
| H | 3-CF₃ | H | 3-CH₃C₆H₄ |
| H | 3-CF₃ | H | 4-CH₃C₆H₄ |
| H | 3-CF₃ | H | 2-OCH₃C₆H₄ |
| H | 3-CF₃ | H | 3-OCH₃C₆H₄ |
| H | 3-CF₃ | H | 4-OCH₃C₆H₄ |
| H | 3-CF₃ | H | 2-CF₃C₆H₄ |
| H | 3-CF₃ | H | 3-CF₃C₆H₄ |
| H | 3-CF₃ | H | 4-CF₃C₆H₄ |
| H | 3-CF₃ | H | 2-NO₂C₆H₄ |
| H | 3-CF₃ | H | 3-NO₂C₆H₄ |
| H | 3-CF₃ | H | 4-NO₂C₆H₄ |
| H | 3-CF₃ | H | 2-CNC₆H₄ |
| H | 3-CF₃ | H | 3-CNC₆H₄ |
| H | 3-CF₃ | H | 4-CNC₆H₄ |
| H | 3-CF₃ | H | 2-SO₃HC₆H₄ |
| H | 3-CF₃ | H | 3-SO₃HC₆H₄ |
| H | 3-CF₃ | H | 4-SO₃HC₆H₄ |
| H | 3-CF₃ | H | OH |
| H | 3-CF₃ | H | OCH₃ |
| H | 3-CF₃ | H | OC₂H₅ |
| H | 3-CF₃ | H | OC₃H₇ |
| H | 3-CF₃ | H | OC₄H₉ |
| H | 3-CF₃ | H | OC₅H₁₁ |
| H | 3-CF₃ | H | OC₆H₁₃ |
| H | 3-CF₃ | H | OAllyl |
| H | 3-CF₃ | H | OPropargyl |
| H | 3-CF₃ | H | OCF₃ |
| H | 3-CF₃ | H | OCCl₃ |
| H | 3-CF₃ | H | OCH₂CH₂F |
| H | 3-CF₃ | H | OCH₂CH₂Cl |
| H | 3-CF₃ | H | OCH₂CF₃ |
| H | 3-CF₃ | H | OCH₂CCl₃ |
| H | 3-CF₃ | H | OC₆H₄ |
| H | 3-CF₃ | H | O(2-FC₆H₄) |
| H | 3-CF₃ | H | O(3-FC₆H₄) |
| H | 3-CF₃ | H | O(4-FC₆H₄) |
| H | 3-CF₃ | H | O(2-ClC₆H₄) |
| H | 3-CF₃ | H | O(3-ClC₆H₄) |
| H | 3-CF₃ | H | O(4-ClC₆H₄) |
| H | 3-CF₃ | H | O(2,3-F₂C₆H₃) |
| H | 3-CF₃ | H | O(2,4-F₂C₆H₃) |
| H | 3-CF₃ | H | O(2,3-Cl₂C₆H₃) |
| H | 3-CF₃ | H | O(2,4-Cl₂C₆H₃) |
| H | 3-CF₃ | H | O(2-CF₃C₆H₄) |
| H | 3-CF₃ | H | O(3-CF₃C₆H₄) |
| H | 3-CF₃ | H | O(4-CF₃C₆H₄) |
| H | 3-CF₃ | H | NH₂ |
| H | 3-CF₃ | H | NHCH₃ |
| H | 3-CF₃ | H | NHC₂H₅ |
| H | 3-CF₃ | H | NHC₃H₇ |
| H | 3-CF₃ | H | NHC₄H₉ |
| H | 3-CF₃ | H | NHC₅H₁₁ |
| H | 3-CF₃ | H | NHC₆H₁₃ |
| H | 3-CF₃ | H | NHAllyl |
| H | 3-CF₃ | H | NHPropargyl |
| H | 3-CF₃ | H | NHCF₃ |
| H | 3-CF₃ | H | NHCCl₃ |
| H | 3-CF₃ | H | NHCH₂CH₂F |
| H | 3-CF₃ | H | NHCH₂CH₂Cl |

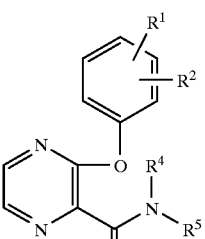

Z = C
    ‖
    O
X = O
n = 0
R³ = H

I.10

| R¹ | R² | R⁴ | R⁵ |
|---|---|---|---|
| H | 3-CF₃ | H | NHCH₂CF₃ |
| H | 3-CF₃ | H | NHCH₂CCl₃ |
| H | 3-CF₃ | H | NHC₆H₄ |
| H | 3-CF₃ | H | NH(2-FC₆H₄) |
| H | 3-CF₃ | H | NH(3-FC₆H₄) |
| H | 3-CF₃ | H | NH(4-C₆H₄) |
| H | 3-CF₃ | H | NH(2-ClC₆H₄) |
| H | 3-CF₃ | H | NH(3-ClC₆H₄) |
| H | 3-CF₃ | H | NH(4-ClC₆H₄) |
| H | 3-CF₃ | H | NH(2,3-F₂C₆H₃) |
| H | 3-CF₃ | H | NH(2,4-F₂C₆H₃) |
| H | 3-CF₃ | H | NH(2,3-Cl₂C₆H₃) |
| H | 3-CF₃ | H | NH(2,4-Cl₂C₆H₃) |
| H | 3-CF₃ | H | NH(2-CF₃C₆H₄) |
| H | 3-CF₃ | H | NH(3-CF₃C₆H₄) |
| H | 3-CF₃ | H | NH(4-CF₃C₆H₄) |
| H | 3-CF₃ | H | (CH₂)₂OH |
| H | 3-CF₃ | H | (CH₂)₂OCH₃ |
| H | 3-CF₃ | H | (CH₂)₂CO₂H |
| H | 3-CF₃ | H | (CH₂)₂CO₂CH₃ |
| H | 3-CF₃ | H | (CH₂)₂CN |
| H | 3-CF₃ | H | (CH₂)₂NH₂ |
| H | 3-CF₃ | H | (CH₂)₂NHCH₃ |
| H | 3-CF₃ | H | (CH₂)₂N(CH₃)₂ |
| H | 3-CF₃ | H | Gly—OtBu |
| H | 3-CF₃ | H | Gly |
| H | 3-CF₃ | H | Ala—OtBu |
| H | 3-CF₃ | H | Ala |
| H | 3-CF₃ | H | Val—OtBu |
| H | 3-CF₃ | H | Val |
| H | 3-CF₃ | H | Phe—OtBu |
| H | 3-CF₃ | H | Phe |
| H | 3-CF₃ | H | Pro—OtBu |
| H | 3-CF₃ | H | Pro |
| H | 3-CF₃ | H | Ser |
| H | 3-CF₃ | H | Ser |
| H | 3-CF₃ | H | Cys |
| H | 3-CF₃ | H | Asp |
| H | 3-CF₃ | H | Tyr |
| H | 3-CF₃ | H | Try |
| H | 3-CF₃ | CH₃ | CH₃ |
| H | 3-CF₃ | CH₃ | C₂H₅ |
| H | 3-CF₃ | CH₃ | n-C₃H₇ |
| H | 3-CF₃ | CH₃ | i-C₃H₇ |
| H | 3-CF₃ | CH₃ | n-C₄H₉ |
| H | 3-CF₃ | CH₃ | s-C₄H₉ |
| H | 3-CF₃ | CH₃ | t-C₄H₉ |
| H | 3-CF₃ | CH₃ | C₅H₁₁ |
| H | 3-CF₃ | CH₃ | C₆H₁₃ |
| H | 3-CF₃ | CH₃ | Allyl |
| H | 3-CF₃ | CH₃ | Propargyl |
| H | 3-CF₃ | CH₃ | Cyclopropyl |
| H | 3-CF₃ | CH₃ | Cyclobutyl |
| H | 3-CF₃ | CH₃ | Cyclopentyl |
| H | 3-CF₃ | CH₃ | Cyclohexyl |
| H | 3-CF₃ | CH₃ | CF₃ |
| H | 3-CF₃ | CH₃ | CCl₃ |
| H | 3-CF₃ | CH₃ | CH₂CCl₃ |
| H | 3-CF₃ | CH₃ | CH₂CH₂F |
| H | 3-CF₃ | CH₃ | CH₂CH₂Cl |
| H | 3-CF₃ | CH₃ | CH₂CF₃ |
| H | 3-CF₃ | CH₃ | CH₂CCl₃ |
| H | 3-CF₃ | CH₃ | C₆H₄ |

-continued

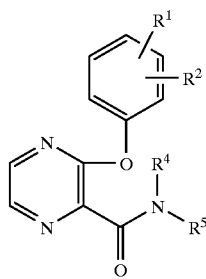

Z = C
X = O
n = 0
R³ = H

I.10

| R¹ | R² | R⁴ | R⁵ |
|---|---|---|---|
| H | 3-CF₃ | CH₃ | 2-FC₆H₄ |
| H | 3-CF₃ | CH₃ | 3-FC₆H₄ |
| H | 3-CF₃ | CH₃ | 4-FC₆H₄ |
| H | 3-CF₃ | CH₃ | 2-ClC₆H₄ |
| H | 3-CF₃ | CH₃ | 3-ClC₆H₄ |
| H | 3-CF₃ | CH₃ | 4-ClC₆H₄ |
| H | 3-CF₃ | CH₃ | 2,3-F₂C₆H₃ |
| H | 3-CF₃ | CH₃ | 2,4-F₂C₆H₃ |
| H | 3-CF₃ | CH₃ | 2,3-Cl₂C₆H₃ |
| H | 3-CF₃ | CH₃ | 2,4-Cl₂C₆H₃ |
| H | 3-CF₃ | CH₃ | 2-CH₃C₆H₄ |
| H | 3-CF₃ | CH₃ | 3-CH₃C₆H₄ |
| H | 3-CF₃ | CH₃ | 4-CH₃C₆H₄ |
| H | 3-CF₃ | CH₃ | 2-OCH₃C₆H₄ |
| H | 3-CF₃ | CH₃ | 3-OCH₃C₆H₄ |
| H | 3-CF₃ | CH₃ | 4-OCH₃C₆H₄ |
| H | 3-CF₃ | CH₃ | 2-CF₃C₆H₄ |
| H | 3-CF₃ | CH₃ | 3-CF₃C₆H₄ |
| H | 3-CF₃ | CH₃ | 4-CF₃C₆H₄ |
| H | 3-CF₃ | CH₃ | 2-NO₂C₆H₄ |
| H | 3-CF₃ | CH₃ | 3-NO₂C₆H₄ |
| H | 3-CF₃ | CH₃ | 4-NO₂C₆H₄ |
| H | 3-CF₃ | CH₃ | 2-CNC₆H₄ |
| H | 3-CF₃ | CH₃ | 3-CNC₆H₄ |
| H | 3-CF₃ | CH₃ | 4-CNC₆H₄ |
| H | 3-CF₃ | CH₃ | 2-SO₃HC₆H₄ |
| H | 3-CF₃ | CH₃ | 3-SO₃HC₆H₄ |
| H | 3-CF₃ | CH₃ | 4-SO₃HC₆H₄ |
| H | 3-CF₃ | CH₃ | OH |
| H | 3-CF₃ | CH₃ | OCH₃ |
| H | 3-CF₃ | CH₃ | OC₂H₅ |
| H | 3-CF₃ | CH₃ | OC₃H₇ |
| H | 3-CF₃ | CH₃ | OC₄H₇ |
| H | 3-CF₃ | CH₃ | OC₅H₁₁ |
| H | 3-CF₃ | CH₃ | OC₆H₁₃ |
| H | 3-CF₃ | CH₃ | OAllyl |
| H | 3-CF₃ | CH₃ | OPropargyl |
| H | 3-CF₃ | CH₃ | OCF₃ |
| H | 3-CF₃ | CH₃ | OCCl₃ |
| H | 3-CF₃ | CH₃ | OCH₂CH₂F |
| H | 3-CF₃ | CH₃ | OCH₂CH₂Cl |
| H | 3-CF₃ | CH₃ | OCH₂CF₃ |
| H | 3-CF₃ | CH₃ | OCH₂CCl₃ |
| H | 3-CF₃ | CH₃ | OC₆H₄ |
| H | 3-CF₃ | CH₃ | O(2-FC₆H₄) |
| H | 3-CF₃ | CH₃ | O(3-FC₆H₄) |
| H | 3-CF₃ | CH₃ | O(4-FC₆H₄) |
| H | 3-CF₃ | CH₃ | O(2-ClC₆H₄) |
| H | 3-CF₃ | CH₃ | O(3-ClC₆H₄) |
| H | 3-CF₃ | CH₃ | O(4-ClC₆H₄) |
| H | 3-CF₃ | CH₃ | O(2,3-F₂C₆H₃) |
| H | 3-CF₃ | CH₃ | O(2,4-F₂C₆H₃) |
| H | 3-CF₃ | CH₃ | O(2,3-Cl₂C₆H₃) |
| H | 3-CF₃ | CH₃ | O(2,4-Cl₂C₆H₃) |
| H | 3-CF₃ | CH₃ | O(2-CF₃C₆H₄) |
| H | 3-CF₃ | CH₃ | O(3-CF₃C₆H₄) |
| H | 3-CF₃ | CH₃ | O(4-CF₃C₆H₄) |
| H | 3-CF₃ | CH₃ | NH₂ |
| H | 3-CF₃ | CH₃ | NHCH₃ |
| H | 3-CF₃ | CH₃ | NHC₂H₅ |
| H | 3-CF₃ | CH₃ | NHC₃H₇ |
| H | 3-CF₃ | CH₃ | NHC₄H₉ |
| H | 3-CF₃ | CH₃ | NHC₅H₁₁ |

-continued

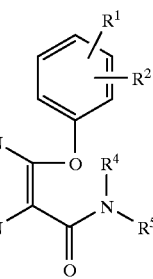

Z = C
X = O
n = 0
R³ = H

I.10

| R¹ | R² | R⁴ | R⁵ |
|---|---|---|---|
| H | 3-CF₃ | CH₃ | NHC₆H₁₃ |
| H | 3-CF₃ | CH₃ | NHAllyl |
| H | 3-CF₃ | CH₃ | NHPropargyl |
| H | 3-CF₃ | CH₃ | NHCF₃ |
| H | 3-CF₃ | CH₃ | NHCCl₃ |
| H | 3-CF₃ | CH₃ | NHCH₂CH₂F |
| H | 3-CF₃ | CH₃ | NHCH₂CH₂Cl |
| H | 3-CF₃ | CH₃ | NHCH₂CF₃ |
| H | 3-CF₃ | CH₃ | NHCH₂CCl₃ |
| H | 3-CF₃ | CH₃ | NHC₆H₄ |
| H | 3-CF₃ | CH₃ | NH(2-FC₆H₄) |
| H | 3-CF₃ | CH₃ | NH(3-FC₆H₄) |
| H | 3-CF₃ | CH₃ | NH(4-C₆H₄) |
| H | 3-CF₃ | CH₃ | NH(2-ClC₆H₄) |
| H | 3-CF₃ | CH₃ | NH(3-ClC₆H₄) |
| H | 3-CF₃ | CH₃ | NH(4-ClC₆H₄) |
| H | 3-CF₃ | CH₃ | NH(2,3-F₂C₆H₃) |
| H | 3-CF₃ | CH₃ | NH(2,4-F₂C₆H₃) |
| H | 3-CF₃ | CH₃ | NH(2,3-Cl₂C₆H₃) |
| H | 3-CF₃ | CH₃ | NH(2,4-Cl₂C₆H₃) |
| H | 3-CF₃ | CH₃ | NH(2-CF₃C₆H₄) |
| H | 3-CF₃ | CH₃ | NH(3-CF₃C₆H₄) |
| H | 3-CF₃ | CH₃ | NH(4-CF₃C₆H₄) |
| H | 3-CF₃ | CH₃ | (CH₂)₂OH |
| H | 3-CF₃ | CH₃ | (CH₂)₂OCH₃ |
| H | 3-CF₃ | CH₃ | (CH₂)₂CO₂H |
| H | 3-CF₃ | CH₃ | (CH₂)₂CO₂CH₃ |
| H | 3-CF₃ | CH₃ | (CH₂)₂CN |
| H | 3-CF₃ | CH₃ | (CH₂)₂NH₂ |
| H | 3-CF₃ | CH₃ | (CH₂)₂NHCH₃ |
| H | 3-CF₃ | CH₃ | (CH₂)₂N(CH₃)₂ |
| H | 3-CF₃ | CH₃ | Gly—OtBu |
| H | 3-CF₃ | CH₃ | Gly |
| H | 3-CF₃ | CH₃ | Ala—OtBu |
| H | 3-CF₃ | CH₃ | Ala |
| H | 3-CF₃ | CH₃ | Val—OtBu |
| H | 3-CF₃ | CH₃ | Val |
| H | 3-CF₃ | CH₃ | Phe—OtBu |
| H | 3-CF₃ | CH₃ | Phe |
| H | 3-CF₃ | CH₃ | Pro—OtBu |
| H | 3-CF₃ | CH₃ | Pro |
| H | 3-CF₃ | CH₃ | Ser |
| H | 3-CF₃ | CH₃ | Cys |
| H | 3-CF₃ | CH₃ | Asp |
| H | 3-CF₃ | CH₃ | Tyr |
| H | 3-CF₃ | CH₃ | Try |
| 2-F | 4-F | H | CH₃ |
| 2-F | 4-F | H | C₂H₅ |
| 2-F | 4-F | H | n-C₃H₇ |
| 2-F | 4-F | H | i-C₃H₇ |
| 2-F | 4-F | H | n-C₄H₉ |
| 2-F | 4-F | H | s-C₄H₉ |
| 2-F | 4-F | H | t-C₄H₉ |
| 2-F | 4-F | H | C₅H₁₁ |
| 2-F | 4-F | H | C₆H₁₃ |
| 2-F | 4-F | H | Allyl |
| 2-F | 4-F | H | Propargyl |
| 2-F | 4-F | H | Cyclopropyl |
| 2-F | 4-F | H | Cyclobutyl |
| 2-F | 4-F | H | Cyclopentyl |
| 2-F | 4-F | H | Cyclohexyl |
| 2-F | 4-F | H | CF₃ |
| 2-F | 4-F | H | CCl₃ |

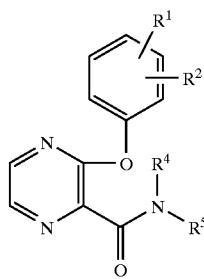

Z = C
O
X = O
n = 0
R³ = H

I.10

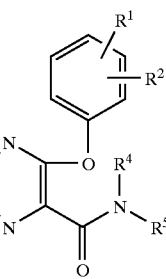

Z = C
O
X = O
n = 0
R³ = H

I.10

| R¹ | R² | R⁴ | R⁵ |
|---|---|---|---|
| 2-F | 4-F | H | CH₂CF₃ |
| 2-F | 4-F | H | CH₂CCl₃ |
| 2-F | 4-F | H | CH₂CH₂F |
| 2-F | 4-F | H | CH₂CH₂Cl |
| 2-F | 4-F | H | CH₂CF₃ |
| 2-F | 4-F | H | CH₂CCl₃ |
| 2-F | 4-F | | CH₂CH₂CH₂ |
| 2-F | 4-F | | CH₂(CH₂)₂CH₂ |
| 2-F | 4-F | | CH₂(CH₂)₃CH₂ |
| 2-F | 4-F | | CH₂(CH₂)₄CH₂ |
| 2-F | 4-F | | (CH₂)₂O(CH₂)₂ |
| 2-F | 4-F | | (CH₂)₂S(CH₂)₂ |
| 2-F | 4-F | | (CH₂)₂NH(CH₂)₂ |
| 2-F | 4-F | | (CH₂)₂NCH₃(CH₂)₂ |
| 2-F | 4-F | H | C₆H₄ |
| 2-F | 4-F | H | 2-FC₆H₄ |
| 2-F | 4-F | H | 3-FC₆H₄ |
| 2-F | 4-F | H | 4-FC₆H₄ |
| 2-F | 4-F | H | 2-ClC₆H₄ |
| 2-F | 4-F | H | 3-ClC₆H₄ |
| 2-F | 4-F | H | 4-ClC₆H₄ |
| 2-F | 4-F | H | 2,3-F₂C₆H₃ |
| 2-F | 4-F | H | 2,4-F₂C₆H₃ |
| 2-F | 4-F | H | 2,3-Cl₂C₆H₃ |
| 2-F | 4-F | H | 2,4-Cl₂C₆H₃ |
| 2-F | 4-F | H | 2-CH₃C₆H₄ |
| 2-F | 4-F | H | 3-CH₃C₆H₄ |
| 2-F | 4-F | H | 4-CH₃C₆H₄ |
| 2-F | 4-F | H | 2-OCH₃C₆H₄ |
| 2-F | 4-F | H | 3-OCH₃C₆H₄ |
| 2-F | 4-F | H | 4-OCH₃C₆H₄ |
| 2-F | 4-F | H | 2-CF₃C₆H₄ |
| 2-F | 4-F | H | 3-CF₃C₆H₄ |
| 2-F | 4-F | H | 4-CF₃C₆H₄ |
| 2-F | 4-F | H | 2-NO₂C₆H₄ |
| 2-F | 4-F | H | 3-NO₂C₆H₄ |
| 2-F | 4-F | H | 4-NO₂C₆H₄ |
| 2-F | 4-F | H | 2-CNC₆H₄ |
| 2-F | 4-F | H | 3-CNC₆H₄ |
| 2-F | 4-F | H | 4-CNC₆H₄ |
| 2-F | 4-F | H | 2-SO₃HC₆H₄ |
| 2-F | 4-F | H | 3-SO₃HC₆H₄ |
| 2-F | 4-F | H | 4-SO₃HC₆H₄ |
| 2-F | 4-F | H | OH |
| 2-F | 4-F | H | OCH₃ |
| 2-F | 4-F | H | OC₂H₅ |
| 2-F | 4-F | H | OC₃H₇ |
| 2-F | 4-F | H | OC₄H₉ |
| 2-F | 4-F | H | OC₅H₁₁ |
| 2-F | 4-F | H | OC₆H₁₃ |
| 2-F | 4-F | H | OAllyl |
| 2-F | 4-F | H | OPropargyl |
| 2-F | 4-F | H | OCF₃ |
| 2-F | 4-F | H | OCCl₃ |
| 2-F | 4-F | H | OCH₂CH₂F |
| 2-F | 4-F | H | OCH₂CH₂Cl |
| 2-F | 4-F | H | OCH₂CF₃ |
| 2-F | 4-F | H | OCH₂CCl₃ |
| 2-F | 4-F | H | OC₆H₄ |
| 2-F | 4-F | H | O(2-FC₆H₄) |
| 2-F | 4-F | H | O(3-FC₆H₄) |
| 2-F | 4-F | H | O(4-FC₆H₄) |
| 2-F | 4-F | H | O(2-ClC₆H₄) |
| 2-F | 4-F | H | O(3-ClC₆H₄) |
| 2-F | 4-F | H | O(4-ClC₆H₄) |
| 2-F | 4-F | H | O(2,3-F₂C₆H₃) |
| 2-F | 4-F | H | O(2,4-F₂C₆H₃) |
| 2-F | 4-F | H | O(2,3-Cl₂C₆H₃) |
| 2-F | 4-F | H | O(2,4-Cl₂C₆H₃) |
| 2-F | 4-F | H | O(2-CF₃C₆H₄) |
| 2-F | 4-F | H | O(3-CF₃C₆H₄) |
| 2-F | 4-F | H | O(4-CF₃C₆H₄) |
| 2-F | 4-F | H | NH₂ |
| 2-F | 4-F | H | NHCH₃ |
| 2-F | 4-F | H | NHC₂H₅ |
| 2-F | 4-F | H | NHC₃H₇ |
| 2-F | 4-F | H | NHC₄H₉ |
| 2-F | 4-F | H | NHC₅H₁₁ |
| 2-F | 4-F | H | NHC₆H₁₃ |
| 2-F | 4-F | H | NHAllyl |
| 2-F | 4-F | H | NHPropargyl |
| 2-F | 4-F | H | NHCF₃ |
| 2-F | 4-F | H | NHCCl₃ |
| 2-F | 4-F | H | NHCH₂CH₂F |
| 2-F | 4-F | H | NHCH₂CH₂Cl |
| 2-F | 4-F | H | NHCH₂CF₃ |
| 2-F | 4-F | H | NHCH₂CCl₃ |
| 2-F | 4-F | H | NHC₆H₄ |
| 2-F | 4-F | H | NH(2-FC₆H₄) |
| 2-F | 4-F | H | NH(3-FC₆H₄) |
| 2-F | 4-F | H | NH(4-C₆H₄) |
| 2-F | 4-F | H | NH(2-ClC₆H₄) |
| 2-F | 4-F | H | NH(3-ClC₆H₄) |
| 2-F | 4-F | H | NH(4-ClC₆H₄) |
| 2-F | 4-F | H | NH(2,3-F₂C₆H₃) |
| 2-F | 4-F | H | NH(2,4-F₂C₆H₃) |
| 2-F | 4-F | H | NH(2,3-Cl₂C₆H₃) |
| 2-F | 4-F | H | NH(2,4-Cl₂C₆H₃) |
| 2-F | 4-F | H | NH(2-CF₃C₆H₄) |
| 2-F | 4-F | H | NH(3-CF₃C₆H₄) |
| 2-F | 4-F | H | NH(4-CF₃C₆H₄) |
| 2-F | 4-F | H | (CH₂)₂OH |
| 2-F | 4-F | H | (CH₂)₂OCH₃ |
| 2-F | 4-F | H | (CH₂)₂CO₂H |
| 2-F | 4-F | H | (CH₂)₂CO₂CH₃ |
| 2-F | 4-F | H | (CH₂)₂CN |
| 2-F | 4-F | H | (CH₂)₂NH₂ |
| 2-F | 4-F | H | (CH₂)₂NHCH₃ |
| 2-F | 4-F | H | (CH₂)₂N(CH₃)₂ |
| 2-F | 4-F | H | Gly—OtBu |
| 2-F | 4-F | H | Gly |
| 2-F | 4-F | H | Ala—OtBu |
| 2-F | 4-F | H | Ala |
| 2-F | 4-F | H | Val—OtBu |
| 2-F | 4-F | H | Val |
| 2-F | 4-F | H | Phe—OtBu |
| 2-F | 4-F | H | Phe |
| 2-F | 4-F | H | Pro—OtBu |
| 2-F | 4-F | H | Pro |
| 2-F | 4-F | H | Ser |
| 2-F | 4-F | H | Cys |
| 2-F | 4-F | H | Asp |
| 2-F | 4-F | H | Tyr |
| 2-F | 4-F | H | Try |
| 2-F | 4-F | CH₃ | CH₃ |
| 2-F | 4-F | CH₃ | C₂H₅ |

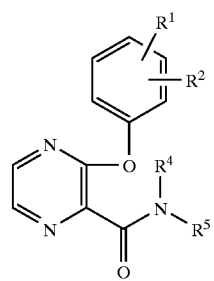

Z = C
X = O
n = 0
R³ = H

I.10

| R¹ | R² | R⁴ | R⁵ |
|---|---|---|---|
| 2-F | 4-F | CH₃ | n-C₃H₇ |
| 2-F | 4-F | CH₃ | i-C₃H₇ |
| 2-F | 4-F | CH₃ | n-C₄H₉ |
| 2-F | 4-F | CH₃ | s-C₄H₉ |
| 2-F | 4-F | CH₃ | t-C₄H₉ |
| 2-F | 4-F | CH₃ | C₅H₁₁ |
| 2-F | 4-F | CH₃ | C₆H₁₃ |
| 2-F | 4-F | CH₃ | Allyl |
| 2-F | 4-F | CH₃ | Propargyl |
| 2-F | 4-F | CH₃ | Cyclopropyl |
| 2-F | 4-F | CH₃ | Cyclobutyl |
| 2-F | 4-F | CH₃ | Cyclopentyl |
| 2-F | 4-F | CH₃ | Cyclohexyl |
| 2-F | 4-F | CH₃ | CF₃ |
| 2-F | 4-F | CH₃ | CCl₃ |
| 2-F | 4-F | CH₃ | CH₂CF₃ |
| 2-F | 4-F | CH₃ | CH₂CCl₃ |
| 2-F | 4-F | CH₃ | CH₂CH₂F |
| 2-F | 4-F | CH₃ | CH₂CH₂Cl |
| 2-F | 4-F | CH₃ | CH₂CF₃ |
| 2-F | 4-F | CH₃ | CH₂CCl₃ |
| 2-F | 4-F | CH₃ | C₆H₄ |
| 2-F | 4-F | CH₃ | 2-FC₆H₄ |
| 2-F | 4-F | CH₃ | 3-FC₆H₄ |
| 2-F | 4-F | CH₃ | 4-FC₆H₄ |
| 2-F | 4-F | CH₃ | 2-ClC₆H₄ |
| 2-F | 4-F | CH₃ | 3-ClC₆H₄ |
| 2-F | 4-F | CH₃ | 4-ClC₆H₄ |
| 2-F | 4-F | CH₃ | 2,3-F₂C₆H₃ |
| 2-F | 4-F | CH₃ | 2,4-F₂C₆H₃ |
| 2-F | 4-F | CH₃ | 2,3-Cl₂C₆H₃ |
| 2-F | 4-F | CH₃ | 2,4-Cl₂C₆H₃ |
| 2-F | 4-F | CH₃ | 2-CH₃C₆H₄ |
| 2-F | 4-F | CH₃ | 3-CH₃C₆H₄ |
| 2-F | 4-F | CH₃ | 4-CH₃C₆H₄ |
| 2-F | 4-F | CH₃ | 2-OCH₃C₆H₄ |
| 2-F | 4-F | CH₃ | 3-OCH₃C₆H₄ |
| 2-F | 4-F | CH₃ | 4-OCH₃C₆H₄ |
| 2-F | 4-F | CH₃ | 2-CF₃C₆H₄ |
| 2-F | 4-F | CH₃ | 3-CF₃C₆H₄ |
| 2-F | 4-F | CH₃ | 4-CF₃C₆H₄ |
| 2-F | 4-F | CH₃ | 2-NO₂C₆H₄ |
| 2-F | 4-F | CH₃ | 3-NO₂C₆H₄ |
| 2-F | 4-F | CH₃ | 4-NO₂C₆H₄ |
| 2-F | 4-F | CH₃ | 2-CNC₆H₄ |
| 2-F | 4-F | CH₃ | 3-CNC₆H₄ |
| 2-F | 4-F | CH₃ | 4-CNC₆H₄ |
| 2-F | 4-F | CH₃ | 2-SO₃HC₆H₄ |
| 2-F | 4-F | CH₃ | 3-SO₃HC₆H₄ |
| 2-F | 4-F | CH₃ | 4-SO₃HC₆H₄ |
| 2-F | 4-F | CH₃ | OH |
| 2-F | 4-F | CH₃ | OCH₃ |
| 2-F | 4-F | CH₃ | OC₂H₅ |
| 2-F | 4-F | CH₃ | OC₃H₇ |
| 2-F | 4-F | CH₃ | OC₄H₉ |
| 2-F | 4-F | CH₃ | OC₅H₁₁ |
| 2-F | 4-F | CH₃ | OC₆H₁₃ |
| 2-F | 4-F | CH₃ | OAllyl |
| 2-F | 4-F | CH₃ | OPropargyl |
| 2-F | 4-F | CH₃ | OCF₃ |
| 2-F | 4-F | CH₃ | OCCl₃ |
| 2-F | 4-F | CH₃ | OCH₂CH₂F |
| 2-F | 4-F | CH₃ | OCH₂CH₂Cl |

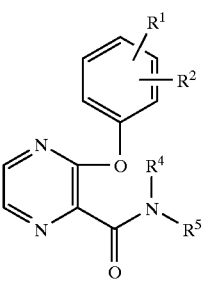

Z = C
X = O
n = 0
R³ = H

I.10

| R¹ | R² | R⁴ | R⁵ |
|---|---|---|---|
| 2-F | 4-F | CH₃ | OCH₂CF₃ |
| 2-F | 4-F | CH₃ | OCH₂CCl₃ |
| 2-F | 4-F | CH₃ | OC₆H₄ |
| 2-F | 4-F | CH₃ | O(2-FC₆H₄) |
| 2-F | 4-F | CH₃ | O(3-FC₆H₄) |
| 2-F | 4-F | CH₃ | O(4-FC₆H₄) |
| 2-F | 4-F | CH₃ | O(2-ClC₆H₄) |
| 2-F | 4-F | CH₃ | O(3-ClC₆H₄) |
| 2-F | 4-F | CH₃ | O(4-ClC₆H₄) |
| 2-F | 4-F | CH₃ | O(2,3-F₂C₆H₃) |
| 2-F | 4-F | CH₃ | O(2,4-F₂C₆H₃) |
| 2-F | 4-F | CH₃ | O(2,3-Cl₂C₆H₃) |
| 2-F | 4-F | CH₃ | O(2,4-Cl₂C₆H₃) |
| 2-F | 4-F | CH₃ | O(2-CF₃C₆H₄) |
| 2-F | 4-F | CH₃ | O(3-CF₃C₆H₄) |
| 2-F | 4-F | CH₃ | O(4-CF₃C₆H₄) |
| 2-F | 4-F | CH₃ | NH₂ |
| 2-F | 4-F | CH₃ | NHCH₃ |
| 2-F | 4-F | CH₃ | NHC₂H₅ |
| 2-F | 4-F | CH₃ | NHC₃H₇ |
| 2-F | 4-F | CH₃ | NHC₄H₉ |
| 2-F | 4-F | CH₃ | NHC₅H₁₁ |
| 2-F | 4-F | CH₃ | NHC₆H₁₃ |
| 2-F | 4-F | CH₃ | NHAllyl |
| 2-F | 4-F | CH₃ | NHPropargyl |
| 2-F | 4-F | CH₃ | NHCF₃ |
| 2-F | 4-F | CH₃ | NHCCl₃ |
| 2-F | 4-F | CH₃ | NHCH₂CH₂F |
| 2-F | 4-F | CH₃ | NHCH₂CH₂Cl |
| 2-F | 4-F | CH₃ | NHCH₂CF₃ |
| 2-F | 4-F | CH₃ | NHCH₂CCl₃ |
| 2-F | 4-F | CH₃ | NHC₆H₄ |
| 2-F | 4-F | CH₃ | NH(2-FC₆H₄) |
| 2-F | 4-F | CH₃ | NH(3-FC₆H₄) |
| 2-F | 4-F | CH₃ | NH(4-C₆H₄) |
| 2-F | 4-F | CH₃ | NH(2-ClC₆H₄) |
| 2-F | 4-F | CH₃ | NH(3-ClC₆H₄) |
| 2-F | 4-F | CH₃ | NH(4-ClC₆H₄) |
| 2-F | 4-F | CH₃ | NH(2,3-F₂C₆H₃) |
| 2-F | 4-F | CH₃ | NH(2,4-F₂C₆H₃) |
| 2-F | 4-F | CH₃ | NH(2,3-Cl₂C₆H₃) |
| 2-F | 4-F | CH₃ | NH(2,4-Cl₂C₆H₃) |
| 2-F | 4-F | CH₃ | NH(2-CF₃C₆H₄) |
| 2-F | 4-F | CH₃ | NH(3-CF₃C₆H₄) |
| 2-F | 4-F | CH₃ | NH(4-CF₃C₆H₄) |
| 2-F | 4-F | CH₃ | (CH₂)₂OH |
| 2-F | 4-F | CH₃ | (CH₂)₂OCH₃ |
| 2-F | 4-F | CH₃ | (CH₂)₂CO₂H |
| 2-F | 4-F | CH₃ | (CH₂)₂CO₂CH₃ |
| 2-F | 4-F | CH₃ | (CH₂)₂CN |
| 2-F | 4-F | CH₃ | (CH₂)₂NH₂ |
| 2-F | 4-F | CH₃ | (CH₂)₂NHCH₃ |
| 2-F | 4-F | CH₃ | (CH₂)₂N(CH₃)₂ |
| 2-F | 4-F | CH₃ | Gly—OtBu |
| 2-F | 4-F | CH₃ | Gly |
| 2-F | 4-F | CH₃ | Ala—OtBu |
| 2-F | 4-F | CH₃ | Ala |
| 2-F | 4-F | CH₃ | Val—OtBu |
| 2-F | 4-F | CH₃ | Val |
| 2-F | 4-F | CH₃ | Phe—OtBu |
| 2-F | 4-F | CH₃ | Phe |
| 2-F | 4-F | CH₃ | Pro—OtBu |
| 2-F | 4-F | CH₃ | Pro |

-continued

I.10

Z = C‖O
X = O
n = 0
R³ = H

| R¹ | R² | R⁴ | R⁵ |
|----|----|----|----|
| 2-F | 4-F | CH₃ | Ser |
| 2-F | 4-F | CH₃ | Cys |
| 2-F | 4-F | CH₃ | Asp |
| 2-F | 4-F | CH₃ | Tyr |
| 2-F | 4-F | CH₃ | Try |

TABLE 9

I.11

Z = C‖O
X = S
n = 0
R³ = H

Compounds of the formula I.11 in which the combination of the radicals $R^1$, $R^2$, $R^4$ and $R^5$ corresponds in each case to a line of the above Table 10 (eg. $R^1$=H, $R^2$=3-CF₃, $R^4$=H and $R^5$=CH₃ etc.).

TABLE 10

I.12

Z = C‖O
X = OCH₂
n = 1
R³ = H

Compounds of the formula I.12 in which the combination of the radicals $R^1$, $R^2$, $R^4$ and $R^5$ corresponds in each case to a line of the above Table 10 (eg. $R^1$=H, $R^2$=3-CF₃, $R^4$=H and $R^5$=CH₃ etc.).

TABLE 11

I.13

Z = C‖S
X = O
n = 0
R³ = H

Compounds of the formula I.13 in which the combination of the radicals $R^1$, $R^2$, $R^4$ and $R^5$ corresponds in each case to a line of the above Table 10 (eg. $R^1$=H, $R^2$=3-CF₃, $R^4$=H and $R^5$ =CH₃ etc.).

TABLE 12

I.14

Z = C‖S
Y = S
n = 0
R³ = H

Compounds of the formula I.14 in which the combination of the radicals $R^1$, $R^2$, $R^4$ and $R^5$ corresponds in each case to a line of the above Table 10 (eg. $R^1$=H, $R^2$=3-CF₃, $R^4$=H and $R^5$=CH₃ etc.).

TABLE 13

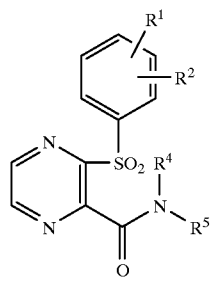

I.15

Z = C
 ‖
 O
X = SO$_2$
n = 0
R$^3$ = H

Compounds of the formula I.15 in which the combination of the radicals R$^1$, R$^2$, R$^4$ and R$^5$ corresponds in each case to a line of the above Table 10 (eg. R$^1$=H, R$^2$=3-CF$_3$, R$^4$=H and R$^5$=CH$_3$ etc.).

TABLE 14

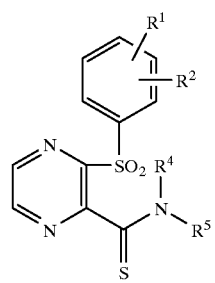

I.16

Z = C
 ‖
 S
X = SO$_2$
n = 0
R$^3$ = H

Compounds of the formula I.16 in which the combination of the radicals R$^1$, R$^2$, R$^4$ and R$^5$ corresponds in each case to a line of the above Table 10 (eg. R$^1$=H, R$^2$=3-CF$_3$, R$^4$=H and R$^5$=CH$_3$ etc.).

TABLE 15

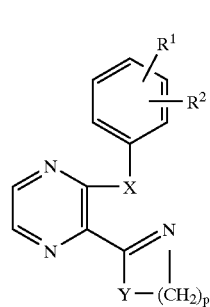

I.17

| R$^1$ | R$^2$ | p | Y | X |
|---|---|---|---|---|
| H | 3-CF$_3$ | 2 | O | O |

TABLE 15-continued

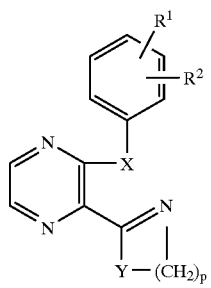

I.17

| R$^1$ | R$^2$ | p | Y | X |
|---|---|---|---|---|
| H | 3-CF$_3$ | 3 | O | O |
| 2-F | 4-F | 2 | O | O |
| 2-F | 4-F | 3 | O | O |
| H | 3-CF$_3$ | 2 | S | O |
| H | 3-CF$_3$ | 3 | S | O |
| 2-F | 4-F | 2 | S | O |
| 2-F | 4-F | 3 | S | O |
| H | 3-CF$_3$ | 2 | O | S |
| H | 3-CF$_3$ | 3 | O | S |
| 2-F | 4-F | 2 | O | S |
| 2-F | 4-F | 3 | O | S |
| H | 3-CF$_3$ | 2 | S | S |
| H | 3-CF$_3$ | 3 | S | S |
| 2-F | 4-F | 2 | S | S |
| 2-F | 4-F | 3 | S | S |

TABLE 16

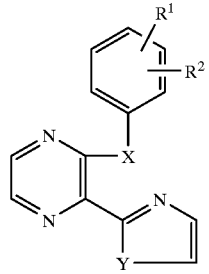

I.18

| R$^1$ | R$^2$ | Y | X |
|---|---|---|---|
| H | 3-CF$_3$ | O | S |
| H | 3-CF$_3$ | O | S |
| 2-F | 4-F | O | S |
| 2-F | 4-F | O | S |
| H | 3-CF$_3$ | S | S |
| H | 3-CF$_3$ | S | S |
| 2-F | 4-F | S | S |
| 2-F | 4-F | S | S |
| H | 3-CF$_3$ | O | O |
| H | 3-CF$_3$ | O | O |
| 2-F | 4-F | O | O |
| 2-F | 4-F | O | O |
| H | 3-CF$_3$ | S | O |
| H | 3-CF$_3$ | S | O |
| 2-F | 4-F | S | O |
| 2-F | 4-F | S | O |

The compounds I and IV or the herbicides containing them, and their environmentally compatible salts of, for example, alkali metals, alkaline earth metals, ammonia or amines, or the herbicides containing them, very effectively control weeds and grass weeds in crops such as wheat, rice, corn, soybean and cotton, without significantly damaging the crops. This effect occurs in particular at low application rates.

In view of the versatility of the application methods, the compounds I and IV or the compositions containing them can also be used in a further number of crops for eliminating undesirable plants. For example, the following crops are suitable: *Allium cepa, Ananas comosus, Arachis hypogaea, Asparagus officinalis, Beta vulgaris* spp. *altissima, Beta vulgaris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spp., *Manihot esculenta, Medicago sativa, Musa* spp., *Nicotiana tabacum* (*N.rustica*), *Olea europaea, Oryza sativa, Phaseolus lunatus, Phaseolus vulgaris, Picea abies, Pinus* spp., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera, Zea mays.*

In addition, the compounds I and IV can also be used in crops which have been made substantially resistant to the action of herbicides by breeding and/or by the use of genetic engineering methods.

The herbicides or the active ingredients can be applied by the preemergence or postemergence method. If the active ingredients are less well tolerated by certain crops, it is possible to use application methods in which the herbicides are sprayed with the aid of the sprayers in such a way that the leaves of the sensitive crops are as far as possible not effected, while the active ingredients reach the leaves of undesirable plants growing underneath or the uncovered soil surface (post-directed, lay-by).

The compounds I and IV or the herbicides containing them can be used, for example, in the form of directly sprayable aqueous solutions, powders, suspensions, including concentrated aqueous, oily or other suspensions or dispersions, emulsions, oil dispersions, pastes, dusting agents, broadcasting agents or granules, by spraying, nebulizing, dusting, broadcasting or pouring. The application forms depend on the intended uses; they should in any case ensure very fine distribution of the novel active ingredients.

Suitable inert assistants for the preparation of directly sprayable solutions, emulsions, pastes or oil dispersions are essentially the following: mineral oil fractions having a medium to high boiling point, such as kerosene or diesel oil, and cold tar oils and oils of vegetable or animal origin, aliphatic, cyclic and aromatic hydrocarbons, for example paraffins, tetrahydronaphthalene, alkylated naphthalenes or derivatives thereof, alkylated benzenes and derivatives thereof, alcohols, such as methanol, ethanol, propanol, butanol and cyclohexanol, ketones, such as cyclohexanone, or strongly polar solvents, for example amines, such as N-methylpyrrolidone, or water.

Aqueous application forms can be prepared from emulsion concentrates, suspensions, pastes, wettable powders or water-dispersible granules by adding water. For the preparation of emulsions, pastes or oil dispersions, the substances, as such or dissolved in an oil or solvent, can be homogenized in water by means of wetting agents, adherents, dispersants or emulsifiers. However, concentrates which consist of active ingredient, wetting agents, adherents, dispersants or emulsifiers and possibly solvents or oil and which are suitable for dilution with water can also be prepared.

Suitable surfactants are alkali metal, alkaline earth metal and ammonium salts of aromatic sulfonic acids, for example lignin-sulfonic, phenolsulfonic, naphthalenesulfonic and dibutylnaphthalenesulfonic acid, and of fatty acids, alkylsulfonates and alkylarylsulfonates, alkylsulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, ligninsulfite waste liquors or methylcellulose.

Powders, broadcasting agents and dusting agents can be prepared by mixing or milling the active ingredients together with a solid carrier.

granules, for example coated, impregnated and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate and ureas, and vegetable products, such as grain flour, bark meal, wood meal and nutshell meal, cellulosic powders and other solid carriers.

The formulations contain in general from 0.01 to 95, preferably from 0.5 to 90, % by weight of active ingredient. The active ingredients are used in a purity of from 90 to 100%, preferably from 95 to 100% (according to the NMR spectrum). The novel compounds I and IV can be formulated, for example, as follows:

I. 20 parts by weight of compound No. 1.002 are dissolved in a mixture which consists of 80 parts by weight of alkylated benzene, 10 parts by weight of the adduct of from 8 to 10 mol of ethylene oxide with 1 mol of N-monoethanololeamide, 5 parts by weight of the calcium salt of dodecylbenzenesulfonic acid and 5 parts by weight of the adduct of 40 mol of ethylene oxide with 1 mol of castor oil. By pouring the solution into 100 000 parts by weight of water and finely distributing it therein, an aqueous dispersion which contains 0.02% by weight of the active ingredient is obtained.

II. 20 parts by weight of compound No. 1.002 are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100 000 parts by weight of water and finely distributing it therein, an aqueous dispersion which contains 0.02% by weight of the active ingredient is obtained.

III. 20 parts by weight of active ingredient No. 1.002 are dissolved in a mixture which consists of 25 parts by weight of cyclohexanone, 65 parts by weight of a mineral oil fraction boiling within a range from 210 to 280° C. and 10 parts by weight of the adduct of 40 mol of ethylene oxide with 1 mol of castor oil. By pouring the solution into a 100 000 parts by weight of water and finely distributing it therein, an aqueous dispersion which contains 0.02% by weight of the active ingredient is obtained.

IV. 20 parts by weight of active ingredient No. 1.002 are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture in 20 000 parts by weight of water, a spray liquor which contains 0.1% by weight of the active ingredient is obtained.

V. 3 parts by weight of active ingredient No. 1.002 are mixed with 97 parts by weight of finely divided kaolin. A dusting agent which contains 3% by weight of the active ingredient is obtained in this manner.

VI. 20 parts by weight of active ingredient No. 1.002 are thoroughly mixed with 2 parts by weight of the calcium salt of dodecylbenzenesulfonic acid, 8 parts by weight of a fatty alcohol polyglycol ether, 2 parts by weight of the sodium salt of a phenol/urea/formaldehyde condensate and 68 parts by weight of a paraffinic mineral oil. A stable oily dispersion is obtained.

In order to broaden the action spectrum and to achieve synergistic effects, the pyrazine derivatives I and IV can be mixed with many typical members of other groups of herbicidal or growth-regulating active ingredients and can be applied together with them. Suitable components for the mixture are, for example, diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which carry, for example, a carboxyl or carbimino group in the 2-position, quinolinecarboxylic acid derivatives, imidazolinones, sulfonamides, sulfonylureas, aryl- oxy- and hetaryloxyphenoxypropionic acids and their salts, esters and amides and others.

It may also be useful to apply the compounds I, alone or in combination with other herbicides, also as a mixture with further crop protection agents, for example with pesticides or compositions for controlling phytopathogenic fungi or bacteria. The miscibility with mineral salt solutions which are used for eliminating nutrient and trace element deficiencies is also of interest. Nonphytotoxic oils and oil concentrates may also be added.

The application rates of active ingredient are from 0.001 to 3, preferably from 0.01 to 1, kg/ha of active ingredient (a.i.), depending on the aim of control, the season, the target plants and the stage of growth.

SYNTHESIS EXAMPLES

Example 1

Synthesis of 2-(3-trifluoromethylphenoxy)-3-cyanopyrazine 12.8 g (80 mmol) of 3-trifluoromethylphenol are added to a suspension of 2.2 g (90 mmol) of sodium hydride in 40 ml of tetrahydrofuran. The reaction mixture is heated to the boil. After 1 hour, a solution of 11.2 g (80 mmol) of 2-chloro-3-cyanopyrazine in 40 ml of tetrahydrofuran is added and the mixture is heated at the boil for a further 4 hours. After the mixture has cooled to room temperature, the solvent is distilled off under reduced pressure. The residue is taken up in diethyl ether and the solution is extracted with 5% strength, aqueous sodium hydroxide solution, washed with distilled water, dried over magnesium sulfate, filtered and freed from the solvent under reduced pressure. The crude product is purified by chromatography (silica gel, cyclohexane/ethyl acetate 20/1 (v/v)). 4.6 g (51%) of a yellow, crystalline solid of melting point 68–70° C. are obtained.

Example 2

Synthesis of methyl 2-(trifluoromethylphenoxy)pyrazine-3-carboxylate

A stream of dry hydrogen chloride is passed into a solution of 5.3 g (20 mmol) of 2-(trifluoromethylphenoxy)-3-cyanopyrazine in 320 ml of dry methanol at 0° C. until saturation is reached. The reaction mixture is cooled to room temperature and, after 2 hours, 320 ml of distilled water are added. The solution is extracted with diethyl ether and the organic phase is washed with distilled water, dried over magnesium sulfate, filtered and freed from the solvent under reduced pressure. The crude product is purified by chromatography (silica gel, cyclohexane/ethyl acetate 10/1 (v/v)). 2.2 g (37%) of colorless, crystalline solid of melting point 83–85° C. are obtained.

Example 3

Synthesis of 2-(2,4-difluorophenoxy)pyrazine-3-carboxylic acid

A solution of 5.3 g (20 mmol) of methyl 2-(2,4-difluorophenoxy)-3-pyrazinecarboxylate in 50 ml of methanol is treated with 5.6 g (0.1 mol) of potassium hydroxide at room temperature for 2 hours. The reaction mixture is freed from the solvent under reduced pressure and the residue is taken up in distilled water. On acidification to pH 2–3, the 2-(2,4-difluorophenoxy)-3-pyrazinecarboxylic acid is precipitated from the solution.

The precipitate is filtered off, washed with distilled water and dried at 50° C. 3.5 g (80%) of a colorless, crystalline solid of melting point 132–136° C. are obtained.

Example 4

Synthesis of N-(cyclopropyl)-2-(3-trifluoromethylphenoxy)-3-pyrazinecarboxamide (compound 1.001)

0.11 g (2.0 mmol) of cyclopropylamine is added to a suspension of 3.0 g (10 mmol) of methyl 2-(3-trifluoromethylphenoxy)-3-pyrazinecarboxylate, 20 g of 3 Å molecular sieve and 20 g of 5 Å molecular sieve in 240 ml of dry toluene at room temperature. The reaction mixture is refluxed for 6 hours. After the mixture has cooled to room temperature, solid components are filtered off. The filtrate is extracted with 10% strength, aqueous hydrochloric acid, washed with distilled water, dried over magnesium sulfate, filtered and freed from the solvent under reduced pressure. 2.8 g (81%) of a colorless, crystalline solid of melting point 74–77° C. are obtained.

Example 5

Synthesis of N-(2,4-difluorophenyl)-2-(3-trifluoromethylphenoxy)-3-pyrazinecarboxamide (compound 1.002)

N-(2,4-Difluorophenyl)-2-(3-trifluoromethylphenoxy)-3-pyrazinecarboxamide is synthesized according to the method described in Example 6.

Yield 0.8 g (19%); colorless, crystalline solid, mp. 107–109° C.

Example 6
Synthesis of N-(2,4-difluorophenyl)-2-(3-nitrophenylthio)-6-pyrazinecarboxamide (compound 1.003)

7 g (11 mmol) of a 50% strength solution of propane-phosphonic anhydride in dichloromethane are added to a solution of 2.8 g (10 mmol) of 2-(3-nitrophenylthio)-6-pyrazinecarboxylic acid, 3.2 g (25 mmol) of 2,4-difluoroaniline and 3 g (30 mmol) of 4-methylmorpholine in dichloromethane at 0° C. The reaction mixture is heated to room temperature. After 12 hours, the solvent is istilled off under reduced pressure. The residue is taken up in diethyl ether and the solution is extracted with 10% strength, aqueous hydrochloric acid, washed with distilled water and with saturated, aqueous sodium bicarbonate solution, dried over magnesium sulfate, filtered and freed from the solvent under reduced pressure. The crude product is purified by chromatography (silica gel, cyclohexane/ethyl acetate 4/1 (v/v)). Yield 1.6 g (40%); light yellow, crystalline solid, mp. 131–135° C.

Further active ingredients of the general formula I have been prepared in a corresponding manner by reacting the pyrazine derivatives II with amines of the formula III using the method described in Example 6. The resulting compounds of the general formula I are summarized in Table 17:

TABLE 17

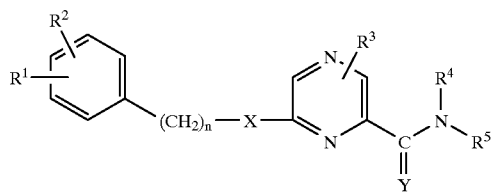

| No. | n | X | Y | $R^1$ | $R^2$ | $R^3$ | $R^4$ | $R^5$ | mp. [° C.] |
|---|---|---|---|---|---|---|---|---|---|
| 1.004 | 0 | O | O | 3-$CF_3H$ | H | H | H | 3-$CF_3C_6H_5$ | 108–113 |
| 1.005 | 0 | O | O | 2-F | 4-F | H | H | n-$C_4H_9$ | |
| 1.006 | 0 | O | O | 2-F | 4-F | H | H | Cyclopropyl | |
| 1.007 | 0 | O | O | 2-F | 4-F | H | H | 2,4-$F_2C_6H_4$ | 165–167 |
| 1.008 | 0 | O | O | 2-F | 4-F | H | H | 3-$CF_3C_6H_5$ | 159–161 |
| 1.009 | 0 | O | O | 2-F | 4-F | H | H | $CH_2CF_3$ | 113–115 |
| 1.010 | 1 | O | O | 2-F | H | H | H | 3-$CF_3C_6H_5$ | 118 |
| 1.011 | 1 | O | O | 2-F | H | H | H | 2,4-$F_2C_6H_4$ | 141 |
| 1.012 | 1 | O | O | 2-F | H | H | H | $CH_2CF_3$ | 71 |
| 1.013 | 1 | O | O | 2-F | H | H | H | Cyclopropyl | 92–96 |

TABLE 18

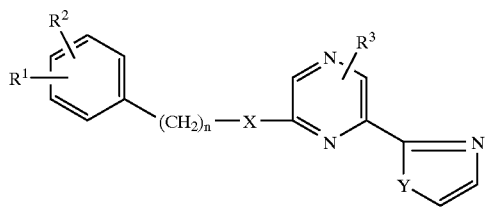

| No. | n | X | Y | $R^1$ | $R^2$ | $R^3$ | $R^4$ | $R^5$ | mp. [° C.] |
|---|---|---|---|---|---|---|---|---|---|
| 1.014 | 0 | S | O | H | H | H | H | n-$C_4H_9$ | oil |
| 1.015 | 0 | S | O | H | H | H | H | $CH_2CF_3$ | 48–50 |

TABLE 18-continued

| No. | n | X | Y | $R^1$ | $R^2$ | $R^3$ | $R^4$ | $R^5$ | mp. [° C.] |
|---|---|---|---|---|---|---|---|---|---|
| 1.016 | 0 | S | O | H | H | H | H | 2,4-$F_2C_6H_3$ | 105–106 |
| 1.017 | 0 | S | O | H | H | H | H | 3-$CF_3C_6H_4$ | 84–85 |
| 1.018 | 0 | S | O | 3-$CF_3$ | H | H | H | n-$C_4H_9$ | oil |
| 1.019 | 0 | S | O | 3-$CF_3$ | H | H | H | $CH_2CF_3$ | 55–56 |
| 1.020 | 0 | S | O | 3-$CF_3$ | H | H | H | 2,4-$F_2C_6H_5$ | 95–96 |
| 1.021 | 0 | S | O | 3-$CF_3$ | H | H | H | 3-$CF_3C_6H_4$ | 100–101 |
| 1.022 | 0 | SO | O | 3-$CF_3$ | H | H | H | 3-$CF_3C_6H_4$ | oil |
| 1.023 | 0 | $SO_2$ | O | 3-$CF_3$ | H | H | H | 3-$CF_3C_6H_4$ | 119–121 |

TABLE 19

| No. | n | X | Y | $R^1$ | $R^2$ | $R^3$ | $R^6$ | mp. [° C.] |
|---|---|---|---|---|---|---|---|---|
| 2.001 | 0 | O | O | 3-$CF_3$ | H | H | 4-$CH_3$ | 81–82 |
| 2.002 | 0 | O | O | 2-F | 4-F | H | 4-$CH_3$ | 98–108 |
| 2.003 | 0 | O | S | 3-$CF_3H$ | H | H | H | 88–92 |

The liquid active ingredients contained in the table have been characterized by IR and NMR spectroscopy. A selection of the most intensive IR bands below 1600 $cm^{-1}$ or the characteristic $^1H$ signals ($\delta$[ppm] in $CDCl_3$) are given below for these compounds.

No. 1.005: 1671, 1506, 1401, 1189
No. 1.006: 1670, 1505, 1402, 1189
No. 1.014: 1528, 1511, 1171, 1128
No. 1.018: 1527, 1322, 1167, 1127
No. 1.022: 1333, 1323, 1126, 1098

Use Examples

The herbicidal action of the pyrazine derivatives of the formulae I and IV could be demonstrated by greenhouse experiments:

The culture vessels used were plastic flower pots containing loamy sand with about 3.0% of humus as a substrate. The seeds of the test plants were sown separately according to species.

In the preemergence treatment, the active ingredients suspended or emulsified in water were applied by means of finely distributing nozzles directly after sowing. The vessels were lightly sprinkler-irrigated in order to promote germination and growth and then covered with transparent plastic covers until the plants had begun to grow. This covering ensures uniform germination of the test plants, unless this has been adversely effected by the active ingredients.

For the postemergence treatment, the test plants were first grown to a height of growth of from 3 to 15 cm, depending on the form of growth, and only thereafter treated with the active ingredients suspended or emulsified in water. For this purpose, the test plants were either directly sown and grown in the same vessels or they were first grown separately as seedlings and transplanted into the test vessels a few days before the treatment. The application rate for the postemergence treatment was 0.5 and 0.25 kg/ha of a.i.

The plants were kept at 10–25° C. or 20–35° C., according to species. The experimental period extended over from 2 to 4 weeks. During this time, the plants were tended and their reaction to the individual treatments was evaluated.

Evaluation was based on a scale from 0 to 100. 100 means no emergence of the plants or complete destruction of at least the above-ground parts and 0 means no damage or normal course of growth.

The plants used in the greenhouse experiments consisted of the following species:

| Botanical name | Common name |
| --- | --- |
| Chenopodium album | lambsquarters (goosefoot) |
| Galium aparine | catchweed bedstraw |
| Sinapis alba | white mustard |
| Setaria viridis | green foxtail |

At an application rate of 0.25 or 0.5 kg/ha of a.i., undesirable plants can be very effectively controlled with the compound from Example 1.002 by the postemergence or preemergence method.

We claim:

1. A method for controlling undesirable plant growth, wherein the undesirable plants or their habitat are or is treated with a herbicidal amount of a substituted pyrazine of the formula IV

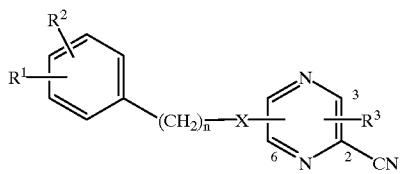

(IV)

where

X is an oxygen or sulfur atom or a sulfoxyl or sulfonyl group;

n is 0, 1 or 2;

$R^1$ and $R^2$ are identical or different and, independently of one another are each hydrogen, $C_1$–$C_{12}$-alkyl, $C_2$–$C_{12}$-alkenyl, $C_2$–$C_{12}$-alkynyl or phenyl, where the phenyl group may be monosubstituted or polysubstituted by a low molecular weight radical selected from the group consisting of alkyl, alkenyl, alkynyl, hydroxyl, alkoxy, alkenyloxy, alkynyloxy, alkoxycarbonyl, aminocarbonyl, mono- and dialkylamido and mono- and diarylamido and N-alkyl-N-arylamido, where the alkyl and aryl radicals may be identical or different, halogen, haloalkyl, haloalkoxy, mercapto, alkylthio, alkenylthio, alkynylthio, haloalkylthio, amino, mono- and dialkylamino, N-alkyl-N-arylamino and mono- and diarylamino, where the alkyl and aryl radicals may be identical or different, sulfonyl- and sulfinylalkyl and sulfonyl- and sulfinyaryl, alkoxycarbonylamino, cyano and nitro;

a five-membered or six-membered heteroaromatic ring selected from the group consisting of pyridine, pyrimidine, furan, pyrrole, pyrazole, imidazole, oxazole, isoxazole, thiazole, isothiazole or thiophene, which heteroaromatic ring may carry one of the abovementioned low molecular weight radicals bonded via a carbon atom;

$C_3$–$C_8$-cycloalkyl or an aralkyl or alkylnaphthyl group, each having 1 to 6 carbon atoms in the alkyl moiety; halogen, $C_1$–$C_{12}$-haloalkyl, hydroxyl, $C_1$–$C_{12}$-alkoxy, $C_1$–$C_{12}$-haloalkoxy, $C_2$–$C_{12}$-alkenyloxy, $C_2$–$C_{12}$-alkynyloxy, mercapto, $C_1$–$C_{12}$-alkylthio, $C_2$–$C_{12}$-alkenylthio, $C_2$–$C_{12}$-alkynylthio, $C_1$–$C_6$-alkoxycarbonyl, amino, $C_1$–$C_6$-mono- or dialkyl- or mono- or diarylamino or N-alkyl-N-arylamino, where the alkyl and aryl radicals may be identical or different, $C_1$–$C_6$-mono- or dialkyl- or mono- or diarylamido or N-alkyl-N-arylamido, where the alkyl and aryl radicals may be identical or different; or $C_1$–$C_6$-alkylsulfonyl or $C_1$–$C_6$-alkylsulfinyl, arylsulfonyl or arylsulfinyl, cyano or nitro;

$R^3$ is hydrogen or is a radical that is present only once and is selected from the group consisting of halogen, $C_1$–$C_{12}$-alkyl, $C_1$–$C_{12}$-haloalkyl, hydroxyl, $C_1$–$C_{12}$-alkoxy, mercapto, $C_1$–$C_{12}$-alkylthio, amino, mono-, dialkylamino, mono-, diarylamino, and N-alkyl-N-arylamino, each of which has 1 to 6 carbon atoms per alkyl radical.

2. A substituted pyrazine of the formula I

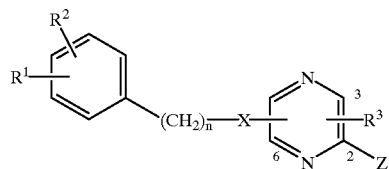

(I)

where

X is an oxygen or sulfur atom or a sulfoxyl or sulfonyl group;

n is 0, 1 or 2;

$R^1$ and $R^2$ are identical or different and, independently of one another are each hydrogen, $C_1$–$C_{12}$-alkyl, $C_2$–$C_{12}$-alkenyl, $C_2$–$C_{12}$-alkynyl or phenyl, where the phenyl group may be monosubstituted or polysubstituted by a low molecular weight radical selected from the group consisting of alkyl, alkenyl, alkynyl, hydroxyl, alkoxy, alkenyloxy, alkynyloxy, alkoxycarbonyl, aminocarbonyl, mono- and dialkylamido and mono- and diarylamido and N-alkyl-N-arylamido, where the alkyl and aryl radicals may be identical or different, halogen, haloalkyl, haloalkoxy, mercapto, alkylthio, alkenylthio, alkynylthio, haloalkylthio, amino, mono- and dialkylamLno, N-alkyl-N-arylamino and mono- and diarylamino, where the alkyl and aryl radicals may be identical or different, sulfonyl- and sulfinylalkyl and sulfonyl- and sulfinylaryl, alkoxycarbonylamino, cyano and nitro;

a five membered or six-membered heteroaromatic ring selected from the group consisting of pyridine, pyrimidine, furan, pyrrole, pyrazole, imidazole, oxazole, isoxazole, thiazole, isothiazole or thiophene, which heteroaromatic ring may carry one of the abovementioned low molecular weight radicals bonded via a carbon atom;

$C_3$–$C_8$-cycloalkyl or an aralkyl or alkylnaphthyl group, each having 1 to 6 carbon atoms in the alkyl moiety;

halogen, $C_1$–$C_{12}$-haloalkyl, hydroxyl, $C_1$–$C_{12}$-alkoxy, $C_1$–$C_{12}$-haloalkoxy, $C_2$–$C_{12}$-alkenyloxy, $C_2$–$C_{12}$-alkynyloxy, mercapto, $C_1$–$C_{12}$-alkylthio, $C_2$–$C_{12}$-alkenylthio, $C_2$–$C_{12}$-alkynylthio, $C_1$–$C_6$-alkoxycarbonyl, amino, $C_1$–$C_6$-mono- or dialkyl- or mono- or diarylamino or N-alkyl-N-arylamino, where the alkyl and aryl radicals may be identical or different, $C_1$–$C_6$-mono- or dialkyl- or mono- or diarylamido or N-alkyl-N-arylamido, where the alkyl and aryl radicals may be identical or different; or $C_1$–$C_6$-alkylsulfonyl or $C_1$–$C_6$-alkylsulfinyl, arylsulfonyl or arylsulfinyl, cyano or nitro;

$R^3$ is one radical selected from the group consisting of hydrogen, halogen, $C_1$–$C_{12}$-alkyl, $C_1$–$C_{12}$-haloalkyl, hydroxyl, $C_1$–$C_{12}$-alkoxy, mercapto, $C_1$–$C_{12}$-alkylthio, amino, mono-, dialkylamino, mono-, diarylamino, and N-alkyl-N-arylamino, each of which has 1 to 6 carbon atoms per alkyl radical; and

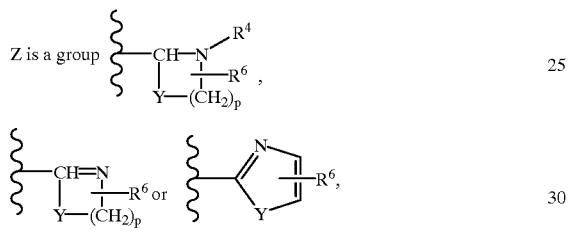

where Y is oxygen or sulfur, p is 2 or 3 and $R^6$ is hydrogen, $C_1$–$C_4$-alkyl, $C_1$–$C_4$-alkoxy, halogen or $C_1$–$C_4$-haloalkyl;

$R^4$ is hydrogen, $C_1$–$C_{12}$-alkyl, $C_2$–$C_{12}$-alkenyl, $C_2$–$C_{12}$-alkynyl or phenyl, where the phenyl group may be monosubstituted or polysubstituted by a low molecular weight radical selected from the group consisting of alkyl, alkenyl, alkynyl, hydroxyl, alkoxy, alkenyloxy, alkynyloxy, alkoxycarbonyl, aminocarbonyl, mono- and dialkylamino and mono- and diarylamino and N-alkyl-N-arylamino, where the alkyl and aryl radicals may be identical or different, halogen, haloalkoxy, mercapto, alkylthio, alkenylthio, alkynylthio, haloalkylthio, amino, mono- and dialkylamino, N-alkyl-N-arylamino and mono- and diarylamino, where the alkyl and aryl radicals may be identical or different, sulfonyl- and sulfinylalkyl and sulfonyl- and sulfinylaryl, alkoxycarbonylamino, cyano and nitro;

$C_3$–$C_8$-cycloalkyl, $C_5$–$C_8$-cycloalkenyl or phenyl-$C_1$–$C_4$-alkyl, where the phenyl group in turn may be monosubstituted or polysubstituted by a low molecular weight radical as stated above;

halogen, $C_1$–$C_{12}$-haloalkyl, $C_2$–$C_{12}$-haloalkenyl or $C_2$–$C_{12}$-haloalkynyl;

where alkyl, alkenyl and alkynyl, alone or as a constituent of other radicals, unless stated otherwise, are radicals having up to 8 carbon atoms and aryl is unsubstituted or substituted phenyl and naphthyl; and agriculturally useful salts of the compound I.

3. The pyrazine of the formula I as defined in claim 2, where $R^3$ and $R^4$ are each hydrogen.

4. A herbicide which contains a substituted pyrazine of the formula I as defined in claim 2 and conventional inert additives.

5. A method for controlling undesirable plant growth, wherein the undesirable plants or their habitat are or is treated with a herbicidal amount of a substituted pyrazine of the formula I as defined in claim 2.

6. A pyrazine of the formula I

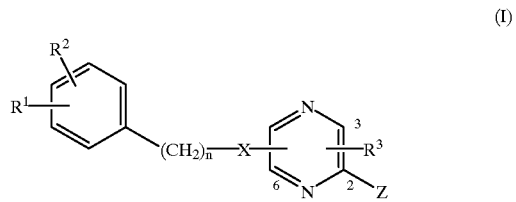

where

X is an oxygen atom;

n is 1 or 2;

$R^1$ and $R^2$ are identical or different and, independently of one another are each hydrogen, $C_1$–$C_{12}$-alkyl, $C_2$–$C_{12}$-alkenyl, $C_2$–$C_{12}$-alkynyl or phenyl, where the phenyl group may be monosubstituted or polysubstituted by a low molecular weight radical selected from the group consisting of alkyl, alkenyl, alkynyl, hydroxyl, alkoxy, alkenyloxy, alkynyloxy, alkoxycarbonyl, aminocarbonyl, mono- and dialkylamido and mono- and diarylamido and N-alkyl-N-arylamido, where the alkyl and aryl radicals may be identical or different, halogen, haloalkyl, haloalkoxy, mercapto, alkylthio, alkenylthio, alkynylthio, haloalkylthio, amino, mono- and dialkylamino, N-alkyl-N-arylamino and mono- and diarylamino, where the alkyl and aryl radicals may be identical or different, sulfonyl- and sulfinylalkyl and sulfonyl- and sulfinylaryl, alkoxycarbonylamino, cyano and nitro;

a five-membered or six-membered heteroaromatic ring selected from the group consisting of pyridine, pyrimidine, furan, pyrrole, pyrazole, imidazole, oxazole, isoxazole, thiazole, isothiazole or thiophene, which heteroaromatic ring may carry one of the abovementioned low molecular weight radicals bonded via a carbon atom;

$C_3$–$C_8$-cycloalkyl or an aralkyl or alkylnaphthyl group, each having 1 to 6 carbon atoms in the alkyl moiety;

halogen, $C_1$–$C_{12}$-haloalkyl, hydroxyl, $C_1$–$C_{12}$-alkoxy, $C_1$–$C_{12}$-haloalkoxy, $C_2$–$C_{12}$-alkenyloxy, $C_2$–$C_{12}$-alkynyloxy, mercapto, $C_1$–$C_{12}$-alkylthio, $C_2$–$C_{12}$-alkenylthio, $C_2$–$C_{12}$-alkynylthio, $C_1$–$C_6$-alkoxycarbonyl, amino, $C_1$–$C_6$-mono- or dialkyl- or mono- or diarylamino or N-alkyl-N-arylamino, where the alkyl and aryl radicals may be identical or different, $C_1$–$C_6$-mono- or dialkyl- or mono- or diarylamido or N-alkyl-N-arylamido, where the alkyl and aryl radicals may be identical or different; or $C_1$–$C_6$-alkylsulfonyl or $C_1$–$C_6$-alkylsulfinyl, arylsulfonyl or arylsulfinyl, cyano or nitro;

$R^3$ is one radical selected from the group consisting of hydrogen, halogen, $C_1$–$C_{12}$-alkyl, $C_1$–$C_{12}$-haloalkyl, hydroxyl, $C_1$–$C_{12}$-alkoxy, mercapto, $C_1$–$C_{12}$-alkylthio, amino, mono-, dialkylamino, mono-, diarylamino, and N-alkyl-N-arylamino, each of which has 1 to 6 carbon atoms per alkyl radical; and Z is a group

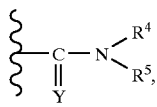

where Y is oxygen or sulfur,

R$^4$ is hydrogen, $C_1$–$C_{12}$-alkyl, $C_2$–$C_{12}$-alkenyl, $C_2$–$C_{12}$-alkynyl or phenyl, where the phenyl group may be monosubstituted or polysubstituted by a low molecular weight radical selected from the group consisting of alkyl, alkenyl, alkynyl, hydroxyl, alkoxy, alkenyloxy, alkynyloxy, alkoxycarbonyl, aminocarbonyl, mono- and dialkylamino and mono- and diarylamino and N-alkyl-N-arylamino, where the alkyl and aryl radicals may be identical or different, halogen, haloalkoxy, mercapto, alkylthio, alkenylthio, alkynylthio, haloalkylthio, amino, mono- and dialkylamino, N-alkyl-N-arylamino and mono- and diarylamino, where the alkyl and aryl radicals may be identical or different, sulfonyl- and sulfinylalkyl and sulfonyl- and sulfinylaryl, alkoxycarbonylamino, cyano and nitro;

$C_3$–$C_8$-cycloalkyl, $C_5$–$C_8$-cycloalkenyl or phenyl-$C_1$–$C_4$-alkyl, where the phenyl group in turn may be monosubstituted or polysubstituted by a low molecular weight radical as stated above;

halogen, $C_1$–$C_{12}$-haloalkyl, $C_2$–$C_{12}$-haloalkenyl or $C_2$–$C_{12}$-haloalkynyl;

R$^5$ is $C_1$–$C_{12}$-alkyl, $C_2$–$C_{12}$-alkenyl, $C_2$–$C_{12}$-alkynyl or phenyl, where the phenyl group may be monosubstituted or polysubstituted by a low molecular weight radical selected from the group consisting of alkyl, alkenyl, alkynyl, hydrosyl, alkoxy, alkenyloxy, alkynyloxy, alkoxycarbonyl, aminocarbonyl, mono- and dialkylamido and mono- and diarylamido and N-alkyl-N-arylamido, where the alkyl and aryl radicals may be identical or different, halogen, haloalkyl, haloalkoxy, mercapto, alkylthio, alkenylthio, alkynylthio, haloalkylthio, amino, mono- and dialkylamino, N-alkyl-N-arylamino and mono- and diarylamino, where the alkyl and aryl radicals may be identical or different, sulfonyl- and sulfinylalkyl and sulfonyl- and sulfinylaryl, alkoxycarbonylamino, cyano and nitro;

a five-membered or six-membered heteroaromatic ring selected from the group consisting of pyridine, pyrimidine, furan, pyrrole, pyrazole, imidazole, oxazole, isoxazole, thiazole, isothiazole or thiophene, which heteroaromatic ring may carry one of the abovementioned low molecular weight radicals bonded via a carbon atom, or $C_3$–$C_8$-cycloalkyl, or an phenylalkyl group, having 1 to 6 carbon atoms in the alkyl moiety, where the phenyl group in turn may be monosubstituted or polysubstituted by a low molecular weight radical as stated above in the case of R$^4$;

$C_1$–$C_{12}$-haloalkyl, hydroxyl, $C_1$–$C_{12}$-alkoxy, $C_1$–$C_{12}$-haloalkoxy, $C_2$–$C_{12}$-alkenyloxy, $C_2$–$C_{12}$-alkynyloxy, mercapto, $C_1$–$C_{12}$-alkylthio, $C_2$–$C_{12}$-alkenylthio, $C_2$–$C_{12}$-alkynylthio, $C_1$–$C_6$-alkoxycarbonyl, amino or $C_1$–$C_6$-mono- or dialkyl- or mono- or diarylamino or N-alkyl-N-arylamino, where the alkyl and aryl radicals may be identical or different, $C_1$–$C_6$-mono- or dialkyl- or mono- or diarylamido or N-alkyl-N-arylamido, where the alkyl and aryl radicals may be identical or different, $C_3$–$C_6$-cycloalkyl, $C_3$–$C_6$-cycloalkyl-$C_1$–$C_4$-alkyl, $C_5$–$C_8$-cycloalkenyl, phenyl-$C_1$–$C_4$-alkyl, tri-$C_1$–$C_4$-alkylsilyl, $C_1$–$C_4$-alkylcarbonyl-$C_1$–$C_4$-alkoxy, $C_1$–$C_4$-alkylcarbonyl, methylcarbonyl-$C_1$–$C_4$-alkoxy or $C_1$–$C_4$-methylcarbonyl, where the last two radicals may each be substituted at the methylene group by $C_1$–$C_5$-aminoalkyl, $C_1$–$C_5$-hydroxyalkyl, $C_1$–$C_5$-thioalkyl or $C_1$–$C_5$-carboxylalkyl;

R$^4$ and R$^5$ together with the N atom to which they are bonded, form a morpholine, piperidyl, piperazinyl, pyrrolidinyl or pyrrolinyl radical;

where alkyl, alkenyl and alkynyl, alone or as a constituent of other radicals, unless stated otherwise, are radicals having up to 8 carbon atoms and aryl is unsubstituted or substituted phenyl and naphthyl; and agriculturally useful salts of the compound I.

7. The pyrazine of the formula I as defined in claim 6, where R$^3$ and R$^4$ are each hydrogen.

8. The pyrazine of the formula I as defined in claim 6, wherein R$^3$ is one radical selected from the group consisting of halogen, $C_1$–$C_{12}$-haloalkyl, hydroxyl or mercapto.

9. The pyrazine of the formula I as defined in claim 6, wherein R$^3$ is one radical selected from the group consisting of hydrogen, $C_1$–$C_{12}$-alkyl, $C_1$–$C_{12}$-alkoxy, $C_1$–$C_{12}$-alkylthio, amino or mono- or dialkylamino or mono- or diarylamino or N-alkyl-N-arylamino, each of which has 1 to 6 carbon atoms per alkyl radical.

10. The pyrazine of the formula I as defined in claim 6, where $R^5$ is an unsubstituted or substituted $C_1$–$C_6$-alkyl or phenyl group.

11. The pyrazine of the formula I as defined in claim 6, wherein the group

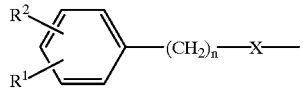

is bonded to the 3-position of the pyrazine ring.

12. The pyrazine of the formula I as defined in claim 6, wherein the group

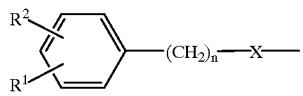

is bonded to the 6-position of the pyrazine ring.

13. A herbicidal composition which comprises a substituted pyrazine of the formula I as defined in claim 6 and a conventional inert additive.

14. A method for controlling undesirable plant growth, wherein the undesirable plants or their habitat are or is treated with a herbicidal amount of a substituted pyrazine of the formula I as defined in claim 6.

15. A pyrazine of the formula I

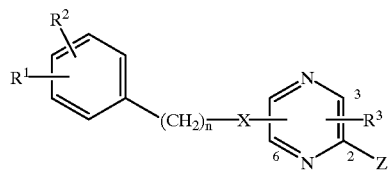

(I)

where

X is a sulfur atom or a sulfoxyl or sulfonyl group;
n is 0, 1 or 2;
$R^1$ is
hydrogen, $C_1$–$C_{12}$-alkyl, $C_2$–$C_{12}$-alkenyl, $C_2$–$C_{12}$-alkynyl or phenyl, where the phenyl group may be monosubstituted or polysubstituted by a low molecular weight radical selected from the group consisting of alkyl, alkenyl, alkynyl, hydroxyl, alkoxy, alkenyloxy, alkynyloxy, alkoxycarbonyl, aminocarbonyl, mono- and dialkylamido and mono- and diarylamido and N-alkyl-N-arylamido, where the alkyl and aryl radicals may be identical or different, halogen, haloalkyl, haloalkoxy, mercapto, alkylthio, alkenylthio, alkynylthio, haloalkylthio, amino, mono- and dialkylamino, N-alkyl-N-arylamino and mono- and diarylamino, where the alkyl and aryl radicals may be identical or different, sulfonyl- and sulfinylalkyl and sulfonyl- and sulfinylaryl, alkoxycarbonylamino, cyano and nitro;
a five-membered or six-membered heteroaromatic ring selected from the group consisting of pyridine, pyrimidine, furan, pyrrole, pyrazole, imidazole, oxazole, isoxazole, thiazole, isothiazole or thiophene, which heteroaromatic ring may carry one of the abovementioned low molecular weight radicals bonded via a carbon atom;
$C_3$–$C_8$-cycloalkyl or an aralkyl or alkylnaphthyl group, each having 1 to 6 carbon atoms in the alkyl moiety;
halogen, $C_1$–$C_{12}$-haloalkyl, hydroxyl, $C_1$–$C_{12}$-haloalkoxy, $C_2$–$C_{12}$-alkenyloxy, $C_2$–$C_{12}$-alkynylozy, mercapto, $C_1$–$C_{12}$-alkylthio, $C_2$–$C_{12}$-alkenylthio, $C_2$–$C_{12}$-alkynylthio, $C_1$–$C_6$-alkoxycarbonyl, amino, $C_1$–$C_6$-mono- or dialkyl- or mono- or diarylamino or N-alkyl-N-arylamino, where the alkyl and aryl radicals may be identical or different, $C_1$–$C_6$-mono- or dialkyl- or mono- or diarylamido or N-alkyl-N-arylamido, where the alkyl and aryl radicals may be identical or different; or
$C_1$–$C_6$-alkylsulfonyl or $C_1$–$C_6$-alkylsulfinyl, arylsulfonyl or arylsulfinyl, cyano or nitro;
$R^2$ is trifluoromethyl or fluorine:
$R^3$ is one radical selected from the group consisting of hydrogen, halogen, $C_1$–$C_{12}$-alkyl, $C_1$–$C_{12}$-haloalkyl, hydroxyl, $C_1$–$C_{12}$-alkoxy, mercapto, $C_1$–$C_{12}$-alkylthio, amino, mono-, dialkylamino, mono-, diarylamino, and N-alkyl-N-arylamino, each of which has 1 to 6 carbon atoms per alkyl radical; and
Z is a group

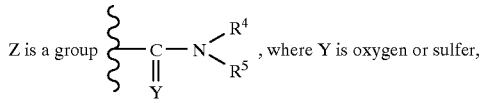, where Y is oxygen or sulfer, where Y is oxygen or sulfur,
$R^4$ is hydrogen, $C_1$–$C_{12}$-alkyl, $C_2$–$C_{12}$-alkenyl, $C_2$–$C_{12}$-alkynyl or phenyl, where the phenyl group may be monosubstituted or polysubstituted by a low molecular weight radical selected from the group consisting of alkyl, alkenyl, alkynyl, hydroxyl, alkoxy, alkenyloxy, alkynyloxy, alkoxycarbonyl, aminocarbonyl, mono- and dialkylamino and mono- and diarylamino and N-alkyl-N-arylamino, where the alkyl and aryl radicals may be identical or different, halogen, haloalkoxy, mercapto, alkylthio, alkenylthio, alkynylthio, haloalkylthio, amino, mono- and dialkylamino, N-alkyl-N-arylamino and mono- and diarylamino, where the alkyl and aryl radicals may be identical or different, sulfonyl- and sulfinylalkyl and sulfonyl- and sulfinylaryl, alkoxycarbonylamino, cyano and nitro;
$C_3$–$C_8$-cycloalkyl, $C_5$–$C_8$-cycloalkenyl or phenyl-$C_1$–$C_4$-alkyl, where the phenyl group in turn may be monosubstituted or polysubstituted by a low molecular weight radical as stated above;
halogen, $C_1$–$C_{12}$-haloalkyl, $C_2$–$C_{12}$-haloalkenyl or $C_2$–$C_{12}$-haloalkynyl;
$R^5$ is $C_1$–$C_{12}$-alkyl, $C_2$–$C_{12}$-alkenyl, $C_2$–$C_{12}$-alkynyl or phenyl, where the phenyl group may be monosubstituted or polysubstituted by a low molecular weight radical selected from the group consisting of alkyl, alkenyl, alkynyl, hydroxyl, alkoxy, alkenyloxy, alkynyloxy, alkoxycarbonyl, aminocarbonyl, mono- and dialkylamido and mono- and diarylamido and N-alkyl-N-arylamido, where the alkyl and aryl radicals may be identical or different, halogen, haloalkyl, haloalkoxy, mercapto, alkylthio, alkenylthio, alkynylthio, haloalkylthio, amino, mono- and dialkylamino, N-alkyl-N-arylamino and mono- and diarylamino, where the alkyl and aryl radicals may be identical or different, sulfonyl- and sulfinylalkyl and sulfonyl- and sulfinylaryl, alkoxycarbonylamino, cyano and nitro;

- a five-membered or six-membered heteroaromatic ring selected from the group consisting of pyridine, pyrimidine, furan, pyrrole, pyrazole, imidazole, oxazole, isoxazole, thiazole, isothiazole or thiophene, which heteroaromatic ring may carry one of the abovementioned low molecular weight radicals bonded via a carbon atom, or
- $C_3$–$C_8$-cycloalkyl, or an phenylalkyl group, having 1 to 6 carbon atoms in the alkyl moiety, where the phenyl group in turn may be monosubstituted or polysubstituted by a low molecular weight radical as stated above in the case of $R^4$;
- $C_1$–$C_{12}$-haloalkyl, $C_1$–$C_{12}$-alkoxy, $C_1$–$C_{12}$-haloalkoxy, $C_2$–$C_{12}$-alkenyloxy, $C_2$–$C_{12}$-alkynyloxy, marcapto, $C_1$–$C_{12}$-alkylthio, $C_2$–$C_{12}$-alkenylthio, $C_2$–$C_{12}$-alkynylthio, $C_1$–$C_6$-alkoxycarbonyl, mono- or diarylamino or N-alkyl-N-arylamino, where the alkyl and aryl radicals may be identical or different, $C_1$–$C_6$-mono- or dialkyl- or mono- or diarylamido or N-alkyl-N-arylamido, where the alkyl and aryl radicals may be identical or different,
- $C_3$–$C_6$-cycloalkyl, $C_3$–$C_6$-cycloalkyl-$C_1$–$C_4$-alkyl, $C_5$–$C_8$-cycloalkenyl, phenyl-$C_1$–$C_4$-alkyl, tri-$C_1$–$C_4$-alkylsilyl, $C_1$–$C_4$-alkylcarbonyl-$C_1$–$C_4$-alkoxy, $C_1$–$C_4$-alkylcarbonyl, methylcarbonyl-$C_1$–$C_4$-alkoxy or $C_1$–$C_4$-methylcarbonyl, where the last two radicals may each be substituted at the methylene group by $C_1$–$C_5$-aminoalkyl, $C_1$–$C_5$-hydroxyalkyl, $C_1$–$C_5$-thioalkyl or $C_1$–$C_5$-carboxylalkyl;
- $R^4$ and $R^5$ together with the N atom to which they are bonded, form a morpholine, piperidyl, piperazinyl, pyrrolidinyl or pyrrolinyl radical;

where alkyl, alkenyl and alkynyl, alone or as a constituent of other radicals, unless stated otherwise, are radicals having up to 8 carbon atoms and aryl is unsubstituted or substituted phenyl and naphthyl; and agriculturally useful salts of the compound I.

16. The pyrazine of the formula I as defined in claim 15, where $R^3$ and $R^4$ are each hydrogen.

17. The pyrazine of the formula I as defined in claim 15, wherein $R^3$ is one radical selected from the group consisting of halogen, $C_1$–$C_{12}$-haloalkyl, hydroxyl or mercapto.

18. The pyrazine of the formula I as defined in claim 15, wherein $R^3$ is one radical selected from the group consisting of hydrogen, $C_1$–$C_{12}$-alkyl, $C_1$–$C_{12}$-alkoxy, $C_1$–$C_{12}$-alkylthio, amino or mono- or dialkylamino or mono- or diarylamino or N-alkyl-N-arylamino, each of which has 1 to 6 carbon atoms per alkyl radical.

19. The pyrazine of the formula I as defined in claim 15, wherein $R^1$ is hydrogen or fluorine.

20. The pyrazine of the formula I as defined in claim 15, wherein $R^1$ is hydrogen and $R^2$ is trifluoromethyl.

21. The pyrazine of the formula I as defined in claim 15, wherein $R^1$ and $R^2$ are fluorine.

22. The pyrazine of the formula I as defined in claim 15, where $R^5$ is an unsubstituted or substituted $C_1$–$C_6$-alkyl or phenyl group.

23. The pyrazine of the formula I as defined in claim 15, wherein the group

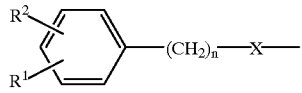

is bonded to the 3-position of the pyrazine ring.

24. The pyrazine of the formula I as defined in claim 15, wherein the group

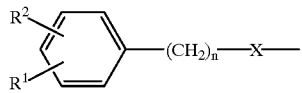

is bonded to the 6-position of the pyrazine ring.

25. A herbicidal composition which comprises a substituted pyrazine of the formula I as defined in claim 15 and a conventional inert additive.

26. A method for controlling undesirable plant growth, wherein the undesirable plants or their habitat are or is treated with a herbicidal amount of a substituted pyrazine of the formula I as defined in claim 15.

* * * * *

UNITED STATES PATENT AND TRADEMARK OFFICE
CERTIFICATE OF CORRECTION

PATENT NO.: 5,939,359

DATED: August 17, 1999

INVENTOR(S): ENGEL et al.

It is certified that error appears in the above-identified patent and that said Letters Patent is hereby corrected as shown below:

Col. 43, claim 1, line 67, "sulfinyaryl" should be --sulfinylaryl--.

Col. 44, claim 2, line 58, "dialkylamLno" should be --dialkylamino--.

Col. 50, claim 15, line 8, "alkynylozy" should be --alkynyloxy--.

Col. 50, claim 15, line 30 after the formula, delete "where Y is oxygen or sulfer,".

Col. 51, claim 15, line 18, "marcapto" should be --mercapto--.

Signed and Sealed this

Fourth Day of January, 2000

Attest:

Attesting Officer

*Acting Commissioner of Patents and Trademarks*